United States Patent
Panasyuk et al.

(10) Patent No.: US 9,204,805 B2
(45) Date of Patent: *Dec. 8, 2015

(54) MEDICAL HYPERSPECTRAL IMAGING FOR EVALUATION OF TISSUE AND TUMOR

(71) Applicant: Hypermed Imaging, Inc., Memphis, TN (US)

(72) Inventors: Svetlana Panasyuk, Lexington, MA (US); Jenny Freeman, Weston, MA (US); Alexander Panasyuk, Lexington, MA (US)

(73) Assignee: Hypermed Imaging, Inc., Memphis, TN (US)

( * ) Notice: Subject to any disclaimer, the term of this patent is extended or adjusted under 35 U.S.C. 154(b) by 297 days.

This patent is subject to a terminal disclaimer.

(21) Appl. No.: 13/678,454

(22) Filed: Nov. 15, 2012

(65) Prior Publication Data

US 2013/0131517 A1     May 23, 2013

Related U.S. Application Data

(63) Continuation of application No. 11/288,410, filed on Nov. 29, 2005, now Pat. No. 8,320,996.

(60) Provisional application No. 60/732,146, filed on Nov. 2, 2005, provisional application No. 60/667,678, filed on Apr. 4, 2005, provisional application No. 60/631,135, filed on Nov. 29, 2004.

(51) Int. Cl.
*A61B 5/00* (2006.01)
*G01J 3/02* (2006.01)
(Continued)

(52) U.S. Cl.
CPC ............. *A61B 5/0091* (2013.01); *A61B 5/0059* (2013.01); *A61B 5/02007* (2013.01);
(Continued)

(58) Field of Classification Search
CPC ...... A61B 5/00; A61B 5/0075; A61B 5/0059; A61B 5/0071
USPC .......................................... 600/407, 473–476
See application file for complete search history.

(56) References Cited

U.S. PATENT DOCUMENTS 4,610,253 A    9/1986   Rosenberg
4,647,918 A    3/1987   Goforth
(Continued)

FOREIGN PATENT DOCUMENTS

WO    WO 2006/058306      6/2006

OTHER PUBLICATIONS

Afromowitz et al., "Multispectral imaging of burn wounds: a new clinical instrument for evaluating burn depth." IEEE Trans Biomed Eng 1988; 35(10):842-50.
(Continued)

*Primary Examiner* — Peter Luong
(74) *Attorney, Agent, or Firm* — Brett A. Lovejoy; Andrew J. Antczak; Morgan, Lewis & Bockius, LLP

(57) ABSTRACT

Apparatus and methods for hyperspectral imaging analysis that assists in real and near-real time assessment of biological tissue condition, viability, and type, and monitoring the above over time. Embodiments of the invention are particularly useful in surgery, clinical procedures, tissue assessment, diagnostic procedures, health monitoring, and medical evaluations, especially in the detection and treatment of cancer.

20 Claims, 12 Drawing Sheets

(51) Int. Cl.

| | |
|---|---|
| *G01J 3/10* | (2006.01) |
| *G01J 3/28* | (2006.01) |
| *G01N 21/21* | (2006.01) |
| *G01N 21/31* | (2006.01) |
| *A61B 5/02* | (2006.01) |
| *G01N 21/35* | (2014.01) |
| *G01N 21/359* | (2014.01) |

(52) U.S. Cl.
CPC ............... *A61B5/415* (2013.01); *A61B 5/416* (2013.01); *A61B 5/418* (2013.01); *A61B 5/4842* (2013.01); *A61B 5/7425* (2013.01); *G01J 3/02* (2013.01); *G01J 3/0224* (2013.01); *G01J 3/0264* (2013.01); *G01J 3/10* (2013.01); *G01J 3/2823* (2013.01); *G01N 21/21* (2013.01); *G01N 21/31* (2013.01); *G01N 21/35* (2013.01); *G01N 21/359* (2013.01); *G01N 2021/317* (2013.01); *G01N 2021/3137* (2013.01); *G01N 2021/3155* (2013.01)

(56) References Cited

U.S. PATENT DOCUMENTS

| | | |
|---|---|---|
| 4,805,016 A | 2/1989 | Kato |
| 4,947,850 A | 8/1990 | Vanderkooi et al. |
| 5,088,503 A | 2/1992 | Seitz |
| 5,349,954 A | 9/1994 | Tiemann et al. |
| 5,438,989 A | 8/1995 | Hochmen et al. |
| 5,539,517 A | 7/1996 | Cabib et al. |
| 5,566,473 A | 10/1996 | Salminen |
| 5,642,096 A | 6/1997 | Leyerer et al. |
| 5,645,081 A | 7/1997 | Argenta et al. |
| 5,722,287 A | 3/1998 | Forstein |
| 5,782,770 A | 7/1998 | Mooradian et al. |
| 5,995,645 A | 11/1999 | Soenksen et al. |
| 6,104,939 A | 8/2000 | Groner et al. |
| 6,122,846 A | 9/2000 | Gray et al. |
| 6,246,301 B1 | 6/2001 | Sogo et al. |
| 6,556,853 B1 | 4/2003 | Cabib et al. |
| 6,587,711 B1 | 7/2003 | Alfano et al. |
| 6,640,130 B1 | 10/2003 | Freeman et al. |
| 6,640,132 B1 | 10/2003 | Freeman et al. |
| 6,728,561 B2 | 4/2004 | Smith et al. |
| 6,741,884 B1 | 5/2004 | Freeman et al. |
| 6,750,964 B2 | 6/2004 | Levenson et al. |
| 6,810,279 B2 | 10/2004 | Mansfield et al. |
| 6,918,883 B2 | 7/2005 | Horton et al. |
| 6,937,885 B1 | 8/2005 | Lewis et al. |
| 7,013,172 B2 | 3/2006 | Mansfield et al. |
| 7,166,852 B2 | 1/2007 | Saracen et al. |
| 7,920,908 B2 | 4/2011 | Hattery et al. |
| 8,320,996 B2 * | 11/2012 | Panasyuk et al. ............. 600/473 |
| 2001/0036304 A1 | 11/2001 | Yang et al. |
| 2002/0055092 A1 | 5/2002 | Hochmen |
| 2002/0057431 A1 | 5/2002 | Fateley et al. |
| 2002/0061142 A1 | 5/2002 | Hiramatsu |
| 2002/0099295 A1 | 7/2002 | Gil et al. |
| 2002/0154300 A1 | 10/2002 | Mansfield et al. |
| 2002/0177894 A1 | 11/2002 | Acosta et al. |
| 2003/0139667 A1 | 7/2003 | Hewko et al. |
| 2004/0111030 A1 | 6/2004 | Zeman |
| 2004/0119020 A1 | 6/2004 | Bodkin et al. |
| 2004/0204651 A1 | 10/2004 | Freeman et al. |
| 2004/0209237 A1 | 10/2004 | Flewelling et al. |
| 2004/0220477 A1 | 11/2004 | Freeman et al. |
| 2005/0049467 A1 | 3/2005 | Stamatas et al. |
| 2006/0241495 A1 | 10/2006 | Kurtz |
| 2006/0247514 A1 | 11/2006 | Panasyuk et al. |
| 2007/0024946 A1 | 2/2007 | Panasyuk et al. |
| 2007/0038042 A1 | 2/2007 | Freeman et al. |
| 2007/0238957 A1 | 10/2007 | Yared |
| 2007/0268485 A1 | 11/2007 | Polonskiy et al. |
| 2009/0216097 A1 | 8/2009 | Wilson et al. |

OTHER PUBLICATIONS

Armstrong et al., "Predicting neuropathic ulceration with infrared dermal thermometry." J Am Podiatr Med Assoc 1997; 87(7):336-7.
Beckert et al,, "The Impact of the Micro-Lightguide O2C for the Quantification of Tissue Ischemia in Diabetic Foot Ulcers." Diabetes Care 2004; 27(12):2863-2867.
Brearley et al., "Peripheral pulse palpation: an unreliable physical sign." Ann R Coll Surg Engl. May 1992; 74(3):169-71.
Caputo et al., "Assessment and management of foot disease in patients with diabetes." N Eng J Med 1994; 331 (13):85460.
Carlson et al., "A historical overview and update on pulse oximetry." Anesthesiol Rev 1993; 20:173-181.
Cavanagh et al., "Correlates of structure and function in neuropathic diabetic feet." Diabetologia 1991; 34(Suppl 2):A39 (abstract).
Colarusso et al., "Infrared spectroscopic imaging: from planetary to cellular systems." Appl Spectrosc 1998; 52:106A-120A.
Dahab, G. et al, "Digital Quantification of Fibrosis in Liver Biopsy Sections: Description of a New Method by Photoshop Software", Journal of Gastroenterology and Hepatology 19:pp. 78-85, 2004.
Dinh et al. "The use of medical hyperspectral technology to evaluate microcirculatory changes in diabetic foot ulcers and predict clinical outcomes." 2007, Diabetes Care:30:903-910.
Dinh et al. "The use of Medical HyperSpectral Imaging (MHSI) to identify patients at risk for developing diabetic foot ulcers." Diabetes 2005;54(SI):A270.
Ferrara et al. "Clinical applications of angiogenic growth factors and their inhibitors". Dec. 1999. Nature Medicine. vol. 5, No. 12: 1359-1364.
Freeman et al., "Medical hyperspectral imaging (MHSI) of 1,2-dimethylbenz(a)-anthracene (DMBA)-induced breast tumors in rats." Poster #1001. In: 27th Annual San Antonio Breast Cancer Symposium; 2004; San Antonio, Texas: Breast Cancer Research and Treatment; 2004. p. S51.
Frykberg et al. "Diabetic foot disorders: a clinical practice guideline. American College of Foot and Ankle Surgeons." J Foot Ankle Surg 2000;39(5 Suppl):SI-60.
Frykberg et al., "Role of neuropathy and high foot pressures in diabetic foot ulceration." Diabetes Care, Oct. 1998;21(10):1714-9.
Frykberg RG. "Diabetic foot ulcers: pathogenesis and management." Am Fam Physician 2002; 66(9): 1655-62.
Gillies et al., "Systemic effects of shock and resuscitation monitored by visible hyper spectral imaging." Diabetes Technol Therapeut 2003; 5(5):847-855.
Greenman et al., "Early changes in the skin microcirculation and muscle metabolism of the diabetic foot." Lancet 2005; 366: 1711-1718.
Harrington et al., "A cost analysis of diabetic lower-extremity ulcers." Diabetes Care 2000; 23(9):1333-8.
Hittel and Donnelly, "Treating peripheral arterial disease in patients with diabetes," Diabetes Obes Metab 2002; 4 Suppl 2:S26-31.
Johnson, William R., et al., Snapshot Hyperspectral Imaging in Ophthalmology, Journal of Biomedical Optics 12(1), 014036 (Jan./Feb. 2007).
Khan and Newton, "Laser Doppler imaging in the investigation of lower limb wounds." Int J Low Extrem Wounds 2003;2(2):74-86.
Lavery and Gazewood, "Assessing the feet of patients with diabetes." J Fam Pract 2000;49(11 Suppl):S9-16.
Lavery et al., "Practical criteria for screening patients at high risk 'For diabetic foot ulceration." Arch Intern Med 1998;158(2):157-62.
Martinez, Luis. "A Non-invasive spectral reflectance method for mapping blood oxygen saturation in wounds". Proceedings of the 31st Applied Imagery Pattern Recognition Workshop 2002; p. 1112.
McMillan DE. "Development of vascular complications in diabetes." Vasc Med 1997; 2(2): 132-42.
Daisuke, Nakao et al., 'Real time multi spectral image processing for mapping pigmentation in human skin' MED Imaging Technol vol. 20, No. 2, 2002, pp. 123-133, XP008142850.
Novo S. "Classification, epidemiology, risk factors, and natural history of peripheral arterial disease." Diabetes Obes Metab 2002; 4 Suppl 2:S1-6.

(56) References Cited

OTHER PUBLICATIONS

Palumbo et al.. "Peripheral vascular disease and diabetes." In: Harris et al. (editors). *Diabetes in America*, 1st ed, Washington, DC: US Government Printing Office; 1985.

Payette et al., "Noninvasive diagnostics: predicting flap viability with near-IR spectroscopy and imaging," Am Clinical Laboratory 1999; 18:4-6.

Pecoraro et al, "Pathways to diabetic limb amputation. Basis for prevention." Diabetes Care 1990; 13(5):513-21.

Rajbhandari et al., Early identification of diabetic foot ulcers that may require intervention using the micro lightguide spectrophotometer, Diabetes Care 1999;22(8): 1292-1295.

Ramsey et al. "Incidence, outcomes, and cost of foot ulcers in patients with diabetes." Diabetes Care 1999; 22(3):382-7.

Reiber et al., "Lower extremity foot ulcers and amputations in diabetes." In: Harris et al. (editors). *Diabetes in America*. 2nd ed. Washington, DC: US Government Printing Office; 1995. p. 402-428.

Riaza et al., "Spectral mapping of rock weathering degrees on granite using hyper spectral DAIS 7915 Spectrometer Data." Internl J Applied Earth Observation and Geoinformation Special issue; Applications of imaging spectroscopy 2001;3-4:345-354.

Sheffield et al., "Laser Doppler Flowmetry." In: *Wound Care Practice*. Flagstaff, AZ. Best Publishing Company; 2004, p. 137.

Sowa et al., "Near infrared spectroscopic assessment of hemodynamic changes in the early post-burn period." Burns 2001;27:241-249.

Sumpio BE. "Foot ulcers." N Engl J Med. Sep. 14, 2000;343(11);787-93.

Sykes and Godsey,"Vascular evaluation of the problem diabetic foot." Clin Podiatr Med Surg 1998; 15(1):49-83.

Thenkabail et al., "Hyperspectral vegetation indices and their relationships with agricultural crop characteristics," Remote Sens Environ 2000;71 (Remote Sens Environ): 158-182.

Treado et al., "Infrared and Raman spectroscopic imaging," Appl Spectrosc Rev 1994;29: 1-38.

van der Laak et al, "Hue-Saturation-Density (HSD) Model for Stain Recognition in Digital imagines from Transmitted Light Spectroscopy" Cytometry 39:pp. 275-284, 2000.

Veves at al. "The Use of Medical HyperSpectral Imaging (MHSI) to evaluate microcirculatory changes and predict clinical outcomes: application to diabetic foot ulcers." Society of Vascular Medicine and Biology 17th Annual Scientific Session 2006(abstract).

Wardlaw et al., "Imaging appearance of the symptomatic perforating artery in patients with lacunar infarction: occlusion or other vascular pathology?", Ann Neurol 2001;50(2):208-15.

Young et al., "The prediction of diabetic neuropathic foot ulceration using vibration perception thresholds. A prospective study." Diabetes Care 1994; 17(6):557-60.

Zamboni et al. "Evaluation of hyperbaric oxygen for diabetic wounds: a prospective study", Undersea Hyper Med 1997; 24(3):175-179.

Zimny at al., "Early detection of microcirculatory impairment in diabetic patients with foot at risk." Diabetes Care 2001; 24(10): 1810-4.

Zuzak et al. "Noninvasive determination of spatially resolved and time-resolved tissue perfusion in humans during nitric oxide inhibition and inhalation by use of a visible-reflectance hyper spectral imaging technique." Circulation 2001; 104:2905-2910.

Mak et al, "State-of-the-art research in lower-limb prosthetic biomechanics-socket interface: a review.", J Rehabil Res Dev. Mar.-Apr. 2001;38(2):161-74.

* cited by examiner

NORMAL         DISEASED

MEDICAL HYPERSPECTRAL IMAGING FOR EVALUATION OF TISSUE AND TUMOR

REFERENCE TO RELATED APPLICATIONS

The present application is a continuation of U.S. patent application Ser. No. 11/288,410 entitled Medical Hyperspectral Imaging for Evaluation of Tissue and Tumor, filed Nov. 29, 2005, which claims priority to U.S. Provisional Patent Application Ser. No. 60/631,135 entitled Hyperspectral Imaging in Medical Applications, filed Nov. 29, 2004, Ser. No. 60/667,678 entitled Hyperspectral Imaging in Breast Cancer, filed on Apr. 4, 2005, and Ser. No. 60/732,146 entitled Hyperspectral Analysis for the Detection of Lymphoma, filed on Nov. 2, 2005, which are hereby incorporated by reference.

FIELD OF THE INVENTION

The invention is directed to a hyperspectral imaging analysis that assists in real and near-real time assessment of biological tissue condition, viability, and type, and monitoring the above over time. Embodiments of the invention are particularly useful in surgery, clinical procedures, tissue assessment, diagnostic procedures, health monitoring, and medical evaluations.

BACKGROUND OF THE INVENTION

In 2005, 212,000 new cases of breast cancer are expected, and approximately 40,000 women will die of the disease.[1] Recent national figures indicate that approximately 45% of patients with breast, cancer undergo primary surgical treatment with mastectomy.[2] The use of breast conserving treatment (lumpectomy and radiation therapy; BCT) is increasing as primary surgical treatment for breast cancer as long term studies have documented the efficacy of BCT.[3] BCT is often followed by systemic therapy with chemotherapy, hormone therapy, or both. A prerequisite for BCT is complete removal of the cancer, documented by negative margins on pathologic evaluation of fee lumpectomy specimen. The presence of positive margins is associated with increased local recurrence (LR) rates, 10-15% vs. 1-10% with negative margins.[4] A competing interest is the preservation of breast tissue to minimise deformity.

The importance of local recurrence is controversial. Early studies suggested that LR does hot translate into death from disease.[4] However, recent data showing lower LR rates and survival benefit by adding radiation therapy to mastectomy for patients with higher stage cancers indicate the potential importance of freedom from local recurrence.[5] In addition, LR contributes to significant local, morbidity, usually requiring a mastectomy. Finally LR contributes to the cost of care and anxiety for the patient. Despite these issues. 20-60% of patients undergoing BCT are found to have positive margins requiring additional surgical procedures, either re-excisional lumpectomies, or mastectomy.[6] These additional procedures result in increased cost, increased anxiety for the patient, and, importantly, a delay in initiation of important systemic chemotherapy or radiation therapy.

Although many patients undergoing excisional breast biopsy are found to not have cancer, the wider use of preoperative core needle biopsy has increased the preoperative diagnosis of invasive breast cancer (SBC) or ductal carcinoma in situ (DOS). At operation, the surgeon attempts to completely resect the cancer with negative microscopic margins, but feces several difficulties, DOS often is associated with grossly normal appearing breast tissue and no mass. Breast cancers presenting as a mass allow the surgeon to feel and see the area to be excised. However, the microscopic extent of disease is difficult to gauge. Frozen section analysis of breast biopsy margins is difficult and unreliable, because the fat content of breast tissue results in difficulty in sectioning frozen specimens. Even after standard tissue preparation over 2 days, one estimate is that more than 1,000 slices of a 2 cm biopsy specimen would be necessary to ensure completely negative, margins. Pathologists have attempted to peel the external surface of a permanently fixed specimen, as one might peel an orange, to evaluate the entirety of the specimen margin. This is difficult, and impractical in most institutions, but also does not provide real time information while the patient is in the operating room.

For all of these reasons, surgeons have adopted several techniques to increase the likelihood of negative margins. They may ink the entire specimen with a single colored ink in the operating room or in the pathology suite with the pathologist. More recently, multiple colored inks have been used to mark the six sides of a cuboid breast specimen. The former method does not allow re-resection of a specific positive margin and results in resection of a larger volume of breast tissue since the cavity side with a positive margin is not known. With both approaches, the ink may creep into crevices, resulting in falsely positive margins. With fee multi-colored approach, inks may run together, resulting in confusion as to the location of a specific positive margin.

Many surgeons perform wide excisions, potentially resulting in significant breast deformity that is added, to by the breast, shrinkage associated with radiation therapy. An effective and widely used method to enhance the likelihood of negative margins requires the surgeon, after excision of the tumor bearing specimen, to take additional slices of breast tissue from the four sides aid deep surface of the open breast cavity, and submit these additional "margins" separately as the final margins. This approach eliminates any confusion as to the location of the margin. When this technique is used, additional cancer is found in 20% of additional margins when the margins of the original specimen were negative.[5] Regardless of the technique, final pathology evaluation may take up to one week. This delay results in patient anxiety and longer time to completion of the patient's surgical treatment. A method for reliable, infra-operative margin evaluation would be of great value for breast cancer surgery.

Sentinel lymph node biopsy (SLNB) has replaced elective lymph node dissection (ELND) of the ipsilateral axilla for patients with invasive breast cancer. Because of fee high negative predictive value of SLNB patients with negative sentinel nodes are spared the need for a complete axillary dissection, with its attendant morbidity and cost. Patients with positive nodes may undergo complete axillary dissection synchronously if a frozen section pathology report is positive. The accuracy of sentinel node evaluation by frozen section is problematic,[6] with a significant false negative risk, when compared to the final report. To avoid giving patients bad news after an initial favorable report, many surgeons avoid frozen section entirely, waiting up to a week for the final pathology evaluation to decide whether a patient needs additional surgery. That additional surgery may take place 1-2 weeks later. Lymph, nodes containing malignant, cells may have altered blood flow, which may fee seen by Hyperspectral imaging. A reliable, real time method which accurately predicts lymph node metastasis would allow synchronous and complete management of the axilla, and reduce or eliminate additional anesthesias and operations.[7]

Lymphomas, which include Hodgkin's disease and noo-Modgkin's lymphoma, are the fifth most common type of cancer diagnosed and the sixth most common cause of cancer death in the United States. Of the two basic lymphoma types, non-Hodgkin's lymphoma is the more common, with 16,000 new cases diagnosed annually.[8] The age-adjusted incidence rate of non-Hodgkin's lymphoma among non-Hispanic white men (the demographic group with the greatest preponderance) is 19.1 per 100*000 and among non-Hispanic white women are 12.0 per 100,000. Not unexpectedly, incidence rates increase with age, with a 5-fold increase from ages 30-54 to 70 and older for non-Hispanic white men, hut 16-fold among Filipino women, the group with the greatest increase. However, leukemia and lymphoma also account for about half of the new cancer cases in children. Preclinical detection and intervention are likely to achieve a reduction in these rates. Patients already treated for lymphoma are at the greatest risk. Significantly, a study of patients monitored intensively for relapse (by physical examination, serum, analysis, chest X-ray, gallium and CT scanning, ultrasound and hone marrow biopsy) determined feat, in 91% of patients, relapse was detected at unscheduled visits for symptomatic disease.[9] Furthermore, standard chemotherapy is effective in only 40% of patients. Clearly, new and more effective measures are needed, such as high resolution hyperspectral imaging of physiologic biomarkers for early detection of relapse.

A method, for now-invasive evaluation of the progression of non-Hodgkin's lymphoma (NHL) and responses to therapy would be highly advantageous, having utility as both a non-destructive animal research, tool, and as a non-invasive clinical tool, which greatly improve diagnostic efficiency. Disease progression can be evaluated in solid tissue such as the spleen and from monitoring leukemic cells in blood and lymph nodes. In addition to monitoring systemic microvascular effects induced by the disease.

Differentiating between types of tissue is useful in the medical and surgical arenas. This includes differentiating between types of normal tissue or between varieties of normal tissue types and distinguishing them from tumor tissue.

SUMMARY OF INVENTION

The present invention overcomes the problems and disadvantages associated with current strategies and designs and provides new tools and methods for defecting and assessing cancer in human tissue.

One embodiment of the invention is directed to a medical instrument comprising a first-stage optic responsive to illumination of a tissue, a spectral separator, one or more polarizers, an imaging sensor, a diagnostic processor, a filter control, interface, and a general-purpose operating module. Preferably, the spectral separator is optically responsive to the first-stage optic and has a control input, the polarizer compiles a plurality of light beams into a plane of polarisation before entering the imaging sensor, the imaging sensor is optically responsive to the spectral separator and has an image data output, the diagnostic processor comprises an image acquisition interface with an Input responsive to the imaging sensor and one or more diagnostic protocol modules wherein each diagnostic protocol module contains a set of instructions for operating the spectral separator and for operating the filter control interface, the filter control interface comprises a control output provided to the control input of the spectral separator, which directs the spectral separator independently of the illumination to receive one or more wavelengths of the illumination to provide multispectral or hyperspectral information as determined by the set of instructions provided by the one or more diagnostic protocol module, and the general-purpose operating module performs filtering and acquiring steps one or more times depending on the set of instructions provided by the one or more diagnostic protocol modules.

The instrument may also comprise a second-stage optic responsive to Illumination of the tissue. Preferably, the one or more wavelengths of illumination is one or a combination of UV, visible, NIR, and IR. In preferred embodiments, the multispectral or hyperspectral information determines one or more of presence of cancer for screening or diagnosis, presence of residual cancer in a surgical excision bed, and cancer progression, preferably wherein the presence of cancer is breast, lymphoma or any cancer readily visualised by hypesspectral imaging. Preferred embodiments include the multispectral or hyperspectral information applied laparoscopically, thoracoscopically, cystoscopically, hysteroscopically, bronchoscopically, or mediastinoscopically to assess presence of tumor, adequacy of surgical resection or nodal or intracavitary spread.

The cancer progression detected may be one of tumor stage grading and microvascular changes in any vascular tissue such as skin, eye, ear, nodularity. The presence of cancer detected may fee one of presence of tumor, presence of residual tumor at margin of resection, lymph node assessment, primary diagnosis, and tumor grade or invasiveness.

Another embodiment is directed to the set of instructions comprising preprocessing the hyperspectral information, building a visual image, defining a region of interest of the tissue, converting all hyperspectral image intensities into units of optical density by taking a negative logarithm of each decimal base, decomposing a spectra for each pixel into several independent components, determining three planes for an RGB pseudo-color image, determining a sharpness factor plane, converting the RGB pseudo-color image to a hue-saturation-value/intensity (HSV/I) image having a plane, scaling the hue-saturation-value/intensity image plane with the sharpness factor plane, converting the hue-saturation-value/intensity image hack to the RGB pseudo-color image, removing outliers beyond a standard deviation and stretching image between 0 and 1 displaying the region of interest in pseudo-colors; and characterizing a metabolic state of fee tissue of interest.

The region of interest may be a region or an entire field of view. Preferably, determining the three planes for an RGB pseudo-color image comprises one or more characteristic features of the spectra. Preferably, determining a sharpness factor plane comprises a combination of the images at different wavelengths, preferably by taking a ratio of a yellow plane in the range of about 550-380 nm to a green plane in the range of about 495-525 nm, or by taking a combination of oxyhemoglobin and deoxyhemoglobin spectral components, or by taking a ratio between a wavelength in the red region in the range 615-710 nm and a wavelength in the yellow region in the range of about 550-580 nm or in the orange region in the range of about 580-815 nm. Preferably, outliers are removed beyond a standard deviation, preferably three standard deviations. The region of interest is displayed in pseudo-colors, performed with one of in combination with a color photo image of a subject, or in addition to a color photo image of a subject or by projecting the pseudo-color image onto the observed surface.

Another embodiment of the invention is directed to a method for detecting cancer in tissue comprising preprocessing the hyperspectral information, building a visual image, defining a region of interest of the tissue, converting all hyperspectral image intensities into units of optical density by taking a negative logarithm, of each, decimal base, decomposing a spectra for each pixel into several independent components, determining three planes for an RGB pseudo-color image, determining a sharpness factor plane, converting the RGB pseudo-color image to a hue-saturation-value/intensity (HSV/I) image having a plane, scaling the hue-saturation-value/intensity image plane with the sharpness factor plane, converting the hue-saturation-value/intensity image hack to the RGB pseudo-color image, removing outliers beyond a standard deviation and stretching image between 0 and 1, displaying the region of interest in pseudo-colors, and characterising a metabolic state of the tissue of interest.

The region, of interest may be a region or an entire field of view. Preferably, determining the three planes for an RGB pseudo-color image comprises one or more characteristic features of die spectra. Preferably, determining a sharpness factor plane comprises a combination of the images at different wavelengths, preferably by taking a ratio of a yellow plane in the range of about 550-580 nm to a green plane its the range of about 495-525 nm, or by taking a combination of oxyhemoglobin and deoxyhemoglobin spectral components, or by taking a ratio between a wavelength in the red region in the range 615-710 nm and a wavelength, in the yellow region in the range of about 550-580 nm or in the orange region in the range of about 580-615 nm. Preferably, outliers are removed beyond a standard deviation, preferably three standard deviations. The region of interest is displayed in pseudo-colors, performed with one of in combination with a color photo image of a subject, or in addition to a color photo image of a subject, or by projecting the pseudo-color image onto the observed surface.

Another embodiment is directed to a medical instrument comprising an image projector, one or more remote lights, a remote control device and a real-time data processing package.

Other embodiments and advantages of the invention are set forth in part in the description, which follows, and in part, may be obvious from, this description, or may be learned from the practice of the invention.

DESCRIPTION OF THE INVENTION

Hyperspectral Imaging System

Figure 1:
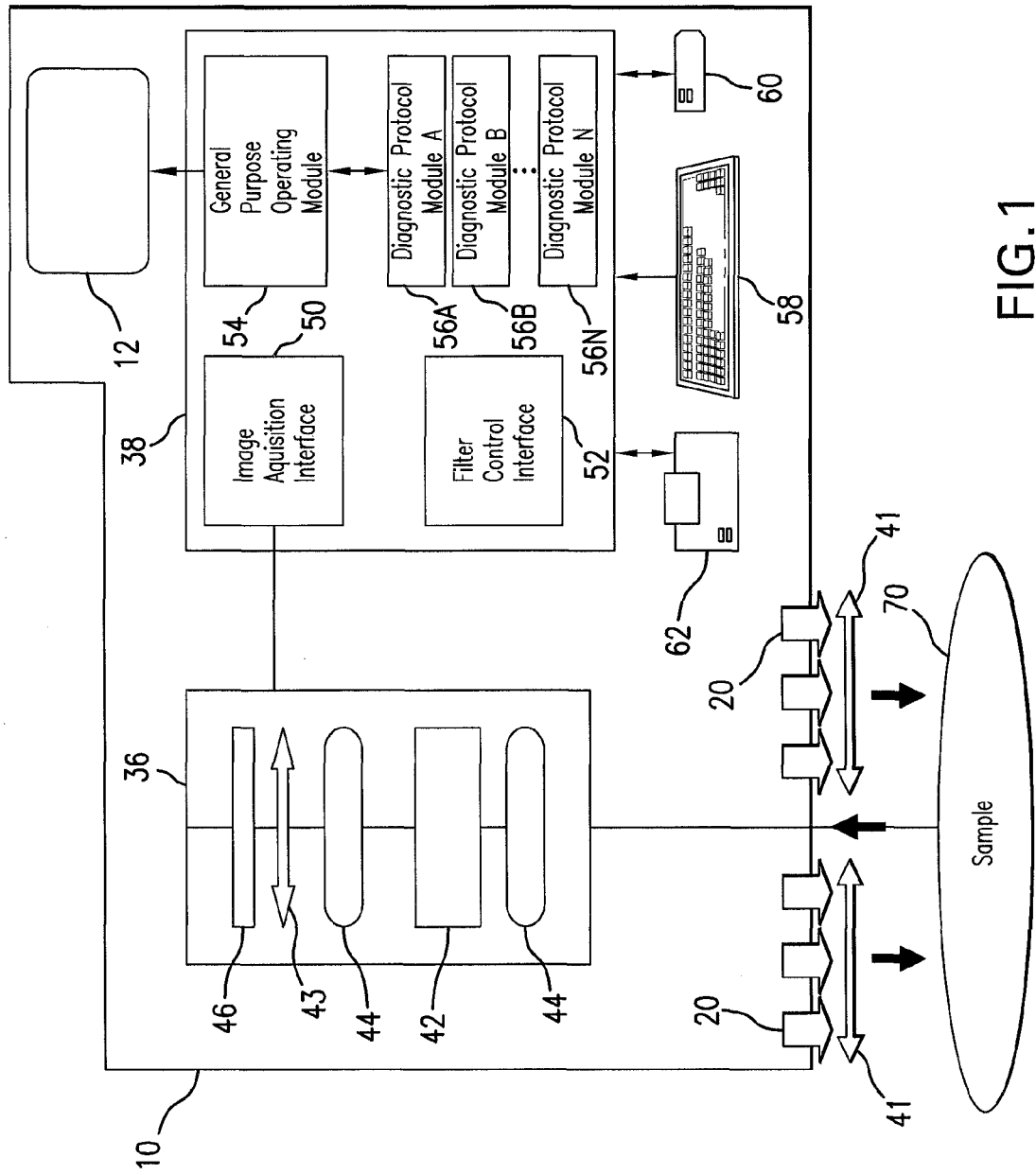
FIG. 1: Block diagram depicting a portable hyperspectral imaging apparatus.

Hyperspectral imaging (HSI) is a novel, method of "imaging spectroscopy" that generates a map of a region of interest based on local chemical composition. HSI has been used in non-medical applications including satellite investigation to indicate areas of chemical weapons production and to assess the condition of agricultural fields, HSI has recently been applied to the investigation of physiologic and pathologic changes in living tissue in animal and human studies to provide information as to the health or disease of tissue that is otherwise unavailable. MHSI has been shown to accurately predict viability and survival of tissue deprived of adequate perfusion, and to differentiate diseased tissue (e.g. tumor) and growth due to cancerous angiogenesis in a rat model system of breast cancer.

HSI is a remote sensing technology in which a 2-dimensional image is created having spectral data inherent in each pixel. These stacks of images comprise what is called a hypercube. It is possible to correlate the spectrum of each pixel with the presence and concentration of various chemical species. This data can than be interpreted as a "gradient map" of these species in a surface. In essence, HSI is a method of "imaging spectroscopy" combining the chemical specificity of spectroscopy with the spatial resolution of imaging.[10] Light is separated into hundreds of wavelengths using a spectral separator and collected on a charge-coupled device (CCD) or a complementary metal oxide semiconductor (CMOS) sensor in much the same way that a picture is taken by an ordinary camera. Used for decades by the military, major airborne applications now are also in mineral exploration and environmental and agricultural, assessments.[11,12,13,14]

Biological tissues also have optical signatures that reflect their chemical characteristics. The primary absorbers in tissue are oxy and deoxy-hemoglohin, hemoglobin breakdown products (e.g. bilirubin and roethemogiohin), melanin, (in skin), lipids and water. The in-vivo absorption spectra of these compounds are well characterized.[15] By comparing collected spectra to standard in-vivo absorption spectra, information about the type, location and relative concentration of chromophores may be quantified.[16,17] The use of MHSI in-vivo provides quantification of several parameters important in the assessment of physiology. These include oxygen delivery, oxygen extraction (correlated with tissue metabolism), total hemoglobin (correlated with perfusion) and water (correlated with tissue edema) with spatial patterns at the level of the microcirculation. Optical scattering also changes in cancerous regions due to an increased number of cells with enlarged nuclei. Scattering from mitotic spindles also increases due to the act that a larger fraction of cells at any one time are undergoing mitosis. We have utilized the spectral and spatial features provided by MHSI to differentiate diseased or cancerous tissue from normal tissue and to deliver information about the "functional anatomy" of the microcirculation associated with local changes due to angiogenesis infection, inflammation, ischemia, and the impact of local tumor metabolism and surrounding tissue response.[18]

HSI has been applied to biomedicine as a non-invasive diagnostic, MHSI is non-contact, camera-based, near-real time, and able to interlace with potential patients a wide variety of settings, either in a diagnostic clinic or as a monitoring tool during surgery. MHSI has been applied toward the early determination of shock, the diagnosis of foot ulcers and foot microcirculation in diabetes, and in the evaluation of resective surgery in breast cancer. MHSI can also utilize local information to evaluate systemic physiology and pathology and has demonstrated this ability in applications such as shock[19,20,21] and progression of diabetes[22].

Significance of Hyperspectral Imaging in Cancer Diagnosis

HSI has the ability to transcend the limitations of the human eye and deliver information present in the electromagnetic spectrum that is otherwise outside the range of our vision (e.g. IR, UV, etc.) and that is beyond the level of our eye to discriminate (e.g. subtle wavelength shifts corresponding to the shifting oxygenation state of hemoglobin). With respect to cancer diagnosis, development of a Hyperspectral Cancer Detection (HCD) system provides quantitative diagnostic information at a time when clinical signs would be nondescript, inconclusive, or simply absent. The early determination of disease onset or progression or the more precise delineation of tumor margins or grade would clearly enhance the power of intervention. As a novel non-invasive, near-real time tool, HCD has the potential to widely impact on the care of the cancer patient.

The present invention uses real time intraoperative margin examination to decrease the time, for completion of surgical, treatment and overall breast cancer treatment. It significantly reduces cost related to operative time and reoperative time as well reducing wait time between procedures. It also reduces patient anxiety waiting to complete their surgical therapy.

MHSI also has potential for margin evaluation with many other tumor types and thus can be applied to many endoscopic procedures, including but not limited to, laparescopy, colonoscopy, thoracoscopy, cystoscopy, hysteroscopy, bronchoscopy, and mediastinoscopy. Skin cancers, including squamous cell and basal cell carcinoma, are treated by local surgical resection with frozen section analysis of the margins. Often, the resection of several additional margins is needed to completely remove the cancer and, daring this time, the surgeon, and patient are idle in the operating room.

Gastrointestinal cancers, such as those of the esophagus and stomach, are known to infiltrate in submucosal planes, at some distance from the main mass. Achieving negative margins at the proximal and distal ends of resection is a standard goal of surgery of these cancers. Real time recognition of residual cancer cells at these margins would reduce operative times. However, real time recognition, is not limited to residual tumors, identification of tumors versus normal tissue cysts is another embodiment of the present invention. The same is said for biliary and pancreatic cancers.

Proper management of sarcomas is contingent upon achieving negative margins. Many patients are found to have microscopically positive margins despite what appears, grossly, to be an adequately wide excision. It has been shown in numerous studies that liver resection for colorectal metastases with positive margins is associated with a much higher recurrence rate and survival than when margins of resection are negative, and in particular, exceed 1 cm.[7]

With pulmonary resection for lung cancer, clearance of the cancer at the bronchial stump margin is necessary. Negative margin excision is critical in the surgical treatment of cancers of the head and neck. At the same time, tissue conservation is critical to reduce the potential resulting deformity. Real time margin assessment would be invaluable.

Spectroscopy is used to assess optical properties (e.g., reflectance, absorbance, scattering) of materials of different composition and state. In medical applications, spectroscopy is widely used for in-vivo measurements that assess the condition of a biological system, such as skin, tissue, or an organ. Once spectroscopy is performed simultaneously over a large area, it is called hyperspectral imaging. A simplified biological multi-spectral imaging apparatus is a human eye that captures reflected light at essentially three wavelength (red, green, and blue) and, once processed by a human brain, allows us to make conclusion about physiological state (e.g., if a person is hot their skirt looks red).

The development of a hyperspectral imaging apparatus for medical applications allows, for expansion of the limitation of a human eye. Now it is possible to acquire reflected light at hundreds of wavelengths under a minute over large areas. As a result, a three dimensional array of data (3D data cube) is obtained, containing an enormous amounts of spatial and spectral information about the sample from which the data was acquired.

Currently, there is no brain-like algorithm that can process vast amounts of spectral data, to facilitate the assessment of physiological conditions such as tissue viability or to make diagnoses or decisions in real life situations such as during surgery or critical care in the emergency room. The volume of information contained in spectroscopic images makes standard data processing techniques time consuming and cumbersome, furthermore, many techniques rely on matching to "learning" curves that require measurement of reference samples (controls) to create a library of spectra to facilitate the identification of chemically related compounds.

The assessment of the metabolic state of tissue is important in areas such as cancer detection, assessing surgical margins, screening for and monitoring diabetes, and for monitoring shock. In many life situations (e.g. operating, emergency room or physician visit room), the assessment of the metabolic state, or physiologic condition is necessary in real-time. That requires a computerized algorithm that pulls out the most critical features from the vast amount of hyperspectral information captured and presents results in an easily assessable color (or pseudo-color) image that, can be interpreted by a person making decisions in the time-pressing environments.

For example, in U.S. Pat. No. 5,782,770 Hyperspectral imaging methods and apparatus for new-invasive diagnosis of tissue for cancer, by Mooradian, et ah, an imaging device is described for capturing hyperspectral images of tissue and specifically for capturing, hyperspectral information that relates to the diagnosis of cancerous tissue.

U.S. Pat. No. 6,640,130 Integrated imaging apparatus, by Freeman, et al., discusses application of a hyperspectral imager such as surgery, clinical procedures, tissue assessment, diagnostic procedures, health monitoring, and other medical valuations, especially when used in combination with other monitors of physiological assessment.

U.S. Pat. No. 6,750,964 Spectral imaging methods and systems, by Levenson and Miller, discusses general, methods of image processing (based on at least one of principal component analysis, projection pursuit, independent component analysis, convex-hull analysis, and machine learning) in application to hyperspectral cubes. In one embodiment, uses reference and target samples to build training tests and therefore cannot be performed in near real-time without preparation. Another disadvantage is that '964 also requires prior library of spectra for different tissue types, classifies each pixel based on correlation to the library samples.

U.S. Pat. No. 6,937,885, Multispectral/Hyperspectral Medical Instrument, by Lewis, et al., describes a medical hyperspectral/multispectral imager for assessing the viability of tissue including the detection or diagnosis of cancer using organ or tissue specific diagnostic protocol modules.

United States Patent Application No. 20010036304 Visualization and processing of multidimensional data using pre-filtering and sorting criteria by Yang, et al, describes a method for handling complex multidimensional datasets generated by digital imaging spectroscopy that allows organization and analysis applying software and computer-based sorting algorithms. The sorting algorithms allow pixels or features from images and graphical data, to be rapidly and efficiently classified into meaningful groups according to defined criteria.

U.S. Pat. No. 6,810,279 Hyperspectral imaging Calibration Device, by Mansfield et al, describes hyperspectral imaging calibration devices and methods for their use that generate images of three dimensional samples.

U.S. Pat. No. 6,640,132 Forensic Hyperspectral Instrument, by Freeman et al. describes portable imaging devices, such as hyperspectral imaging devices, useful for forensic and other analysis, and methods for using these devices. Devices of '132 provide images and patterned data arrays representing images in multiple discrete spectra that can then be summed or processed to allow for detection of patterns or anomalies in the data collected. All of the aforementioned patents are hereby incorporated by reference.

It has surprisingly been discovered that tissues can be assessed specifically for the detection of cancer or tumor beds during surgical excisions, hi the present invention, new methods and tissue specific algorithms are presented that allow the assessment of tissue viability specifically to the detection of cancer, or tumor beds during surgical excision. Cancer detection can include the detection of solid cancers and precancers, and blood borne cancers such as lymphoma. Cancer detection can also include differentiating tumor from, normal, tissue and assessing the malignancy or aggressiveness or "grade" of tumor present. One problem is that often, (e.g. during surgery) it is necessary to assess the tissue composition and oxygenation over a large area and in real or near-real time.

MHSI solves that problem by processing the hyperspectral cubes in near real-time and presenting a high-resolution, pseudo-color image where color varies with tissue type and oxygenation (viability). MHSI consists of fast image processing steps that do not requite prior knowledge of the tissue or its metabolic state, but that can also take additional information from known tumor and tissue into account if so desired.

Another problem is the rapid screening of blood borne, cancer such as lymphoma in real-time without requiring blood draws and histologic assessment MHSI has the ability of assessing microvascular changes in skin due to lymphoma cell loading, MHSI also allows the quantitative monitoring of cancer therapies as a means of optimising treatment on an individual basis or for the exploratory screening and optimization of new drugs. If is also possible that lymphoma or other tumor types may be assessed through the skin by evaluation of an underlying node or solid organ. This may be useful in the staging of disease or in the monitoring of the results of a particular therapeutic regimen.

Yet another problem is that the results of the analysis have to be presented in an easily accessible and interpretable form. MHSI delivers results in a very intuitive form by pairing the MHSI pseudo-color image with the high quality color picture composed from the same hyperspectral data. The identification and assessment of the region of interest (ROI) is easily achieved by flipping between color and MHSI images, and zooming onto the ROI. The images can be seen on a computer screen or projector, and/or stored and transported as any other digital information, and/or printed out. The MHSI image preserves the high resolution of the hyperspectral imager and therefore can be improved with the upgraded hardware.

A fourth problem is that due to the complexity of the biological system, medical personnel want to have as much information as possible about a given case in order to make the most-reliable diagnose. MHSI provides additional information to the doctor that is not currently available and can be used along with other clinical assessments to make this decision. MHSI provides images for further analysis by the human; initially it is not an artificial intelligence decision maker and you would not want to rely directly on the software to make such an important decision, however as more information is gathered, a spectral library compiled and techniques refined, MHSI has the capabilities necessary to be a true diagnostic device.

Additionally, MHSI transcribes vast 3D spectral information into one image preserving biological complexity via millions of color shades. The particular color and distinct shape of features in the pseudo-color image allow discriminate between tissue types such as tumor, connective tissue, muscle, extravasaled blood, and blood vessels. MHSI also allows the near-real time differentiation of tumor grade that will be useful in making appropriate medical decisions.

Yet another problem, is quantifying cancer therapies in order to measure the effectiveness of new therapeutic agents or procedures. MHSI can be used to quantify disease progression in order to identify new therapeutic agents and to develop individual therapeutic regiments depending on how the subject responds to therapy.

MHSI main purposes include 1) expand human eye capabilities beyond the ordinary; 2) expand the human brain capabilities by pro-analyzing the spectral characteristics of the observable subject; 3) perform these tasks with real or near-real time data acquisition. The aim of the algorithm is facilitate the human to diagnose and assess the condition of the observable subject.

MHSI is successful because it is complete, using the spectral data of reflected electro-magnetic radiation (ultraviolet—UY, visible, near infrared—NIR, and infrared—IR), and since different types of tissue reflect, absorb, and scatter light differently, in theory the hyperspectral cubes contains enough information to differentiate between tissue types and conditions. MHSI is robust since it is based on a few general properties of the spectral profiles (slope, offset, and ratio) therefore is pretty flexible with respect to spectral, coverage and is not sensitive to a particular light wavelength, MHSI is fast, because it uses fast image processing techniques that allow superposition of absorbance, scattering, and oxygenation information in one pseudo-color image.

The simplicity of image processing techniques allow for the display of results in real-to-near-real time. MHSI is easily interpretable since it outputs image where color changes according to different tissue types or condition, but the distinction is not a yes/no type, MHSI color scheme allows surgeon to differentiate between different tissue types, in addition, the color and the shape of structures depict different composition and level of viability of the tissue. For example, tumor appears to have an atypical, color and appears as a rounded, almost solid color mass. The blood vessels are rather differentiated by their shape as linear and curvilinear structures (wiggly strings) than by their color per se; the exact color of the vascular structures depends on the blood oxygenation.

Initially, the algorithm needs a person, to conclude that the tissue, is tumor or normal. In another embodiment, a particular color code contains adequate information for diagnosis and are presented as such. In iteration, MHSI by itself is not a definite decision, making algorithm; it is a fool that a medical professional can use in order to give a confident diagnosis, in iteration MHSI contains a decision making algorithm that provides the physician with a diagnosis.

A portable hyperspectral imaging apparatus according to an embodiment of the invention is depicted in FIG. 1. Portable apparatus 10 weighs less than 100 pounds, preferably less than 25 pounds, and more preferably less that 10 pounds. Preferably, the portable apparatus may be battery operated or more preferably, may have a connector adapted to connect to an existing power source.

Portable apparatus 10 comprises an optical acquisition system 36 and a diagnostic processor 38. Optical acquisition system 36 comprises means to acquire broadband data, visible data, ultraviolet data, infra-red data, hyperspectral data, or any combination thereof. In a preferred embodiment, optical acquiring means comprises a first-stage imaging optic 40, a spectral separator 42, a second-stage optic 44, and an imaging sensor 46. Alternatively, optical acquiring means may fee any acquisition system suited for acquiring broadband data, visible data, ultraviolet data, infra-red data, hyperspectral data, or any combination thereof. Preferably, one or more polarizers 41, 43 are included in the acquisition system to compile the light into a plane of polarization before entering the imaging sensor.

If the spectral separator 42 does not internally polarises the light, the first polarizer 43 is placed anywhere in the optical path, preferably in front of the receiving camera 46. The second polarizer 41 is placed in front of illuminating lights (20) such that the incident light polarization is controlled. The incident light is crossed polarized with the light recorded by the camera 46 to reduce specular reflection or polarization at different angles to vary intensity of the reflected light recorded by the camera.

The illumination is provided by the remote light(s) 20, preferably positioned around the light receiving opening of the system. The light can fee a circular array of focused LED lights that emit light at the particular wavelengths (or ranges) that are used In the processing algorithm, or in the ranges of wavelengths (e.g., visible and/or near-infrared). The circular arrangement of the light sources provides even illumination that reduces shadowing. The light wavelength selectivity reduces effect of the observation on the observing subject.

Although the preferred embodiment describes the system, as portable, a non-portable system may also be utilised. Preferably, an optical bead is mounted to the wall of the examination, more preferably, an overhead light structure is located in the operating room, or more preferably, the system has a portable table with an observational window overlooking the operating site.

The first-stage optic receives light collected from a tissue sample through a polarizer and focuses the light onto the surface of the spectral separator. Preferably, the spectral separator is a liquid crystal tunable filter (LCTF). LCTF 42 is a programmable filter that sequentially provides light from selected wavelength bands with small (for example, 7-10 nm) bandwidth from the light collected from the sample. Second-stage optic 44 receives the narrow band of light passing through the spectral separator and focuses the light onto the image sensor 46. The image sensor is preferably, although not necessarily, a two-dimensional array sensor, such as a charge-coupled device array (CCD) or CMOS, which delivers an image signal to the diagnostic processor 38.

Diagnostic processor 38 includes an image acquisition interface 50, that has an input responsive to an output of the image sensor 46 and an output provided to a general-purpose operating module 54. The general-purpose operating module includes routines that perform image processing, and that operates and controls the various parts of the system. The general-purpose operating module also controls the light source(s) (e.g. LED array) allowing for switching on and off during measurement as required by the algorithm. The general-purpose operating module has control output provided to a filter control interface 52, which in turn has an output provided to the spectral separator 42. The general-purpose operating module also interacts with a number of diagnostic protocol modules 56A, 56B, . . . 54N, and has an output provided to a video display. The diagnostic process includes special purpose hardware, general-purpose hardware with special-purpose software, or a combination of the two. The diagnostic processor also includes an input device 58, which is operatively connected to the general-purpose operating module. A storage device 60 and printer 62 also are operatively connected to the general-purpose operating module.

In operation, a portable or semi-portable apparatus is employed near a target, e.g., breast tumor resection bed or general area of interest. An operator begins by selecting a diagnostic protocol module using the input device. Each diagnostic protocol module is adapted to detect particular tissue characteristics of the target. In an alternative embodiment, the apparatus may contain, only one diagnostic module adapted for general medical diagnosis.

Diagnostic processor 38 responds to the operator's input by obtaining a series of transfer functions and an image processing protocol and an image processing protocol from the selected diagnostic protocol module 56. The diagnostic processor provides the filtering transfer functions to the spectral separator 42 via its filter control interface 52 and then instructs the image acquisition interface 50 to acquire and store the resulting filtered image from the image sensor 46. The general-purpose operating module 54 repeats these filtering and acquiring steps one or more times, depending on the number of filter transfer functions stored in the selected diagnostic protocol module. The filtering transfer functions can represent bandpass, multiple bandpass, or other filter characteristics and can include wavelengths in preferably the UV, preferably the visible, preferably the NIR and preferably, the IR electromagnetic spectrum.

In a preferred embodiment, the light source delivering light to the target of interest can be filtered as opposed to the returned light collected by the detector. Thus, a tunable source delivers the information. Alternatively, both a tunable source and a tunable detector may be utilized. Such tuning takes the form of LCTF, acousfo-optical tunable filter (AOTF), filter wheels, matched filters, diffraction gratings or other spectral separators. The light source may be a fiber optic, but is preferably a light emitting diode (LED).

The unique cooling illumination provided by the LED prevents overheating of skin which may result in poor imaging resolution. Preferably, the LED provides sufficient light while producing minimal or no increase in skin temperature. This lighting system in combination with the polarizer allows adequate illumination while preventing surface glare from Internal organs and overheating of skin.

Once the image acquisition interface 50 has stored images for all of the image planes specified by the diagnostic protocol chosen by the operator, the image acquisition interface begins processing these image planes based of the image processing protocol from the selected diagnostic protocol module 56N. Processing operations can include general image processing of combated, images, such as comparing the relative amplitude of the collected light at different wavelengths, adding amplitudes of the collected light at different wavelengths, or computing other combinations of signals corresponding to the acquired planes. The computed image is displayed on the display 12. Other preferred embodiments include storing the computed image in the storage device 60 or printing the computed image out on printer 62.

In an alternative embodiment, diagnostic protocol modules 56, printer 62, display 12, or any combination thereof, may be omitted from portable device 10. In this embodiment, acquired images are stored in storage device 60 daring the medical procedure. At a later time, these images are transferred via a communications link to a second device or computer located at a remote location, for example, hospital medical records, for backup or reviewing at a later time. This second device can have the omitted diagnostic protocol modules, printer, display, or any combination thereof. In another embodiment, the stored images are transferred from portable device 10, located in the clinic, via a communications link to a remote second device in real time.

In a preferred embodiment the system has facility to project real-time hyperspectral data onto the operation field, region of interest, or viewing window positioned above the operating site. The projected information has precise one-to-one mapping to the illuminated surface (e.g. wound, operating surface, tissue) and provides surgeon with necessary information in efficient and non-distractive way. When projected onto an overhang viewing window, the images (real-color and/or pseudo-color) can be zoomed in/out to provide variable magnification. This subsystem consists of the following elements; 1) image projector with field-view precisely co-aligned with the field-of-view of the hyperspectral imager, 2) miniature remote control device which allows surgeon to switch projected image on and off without turning from operation table and change highlight structure and/or translucency on the projected, image to improve visibility of the features of interest as well as projected, image brightness and intensity, 3) real-time data processing package which constructs projected image based on hyperspectral data and operator/surgeon input, 4) optional viewing window positioned above the operating site that is translucent for real observation or opaque for projecting pseudo-color solution or higher resolution images.

To achieve precise co-registration between hyperspectral image and operating surface, the system performs self-alignment procedure before or during the operation as necessary. The system projects a sequence of calibration pattern on the operating surface using projector and reads them using hyperspectral imaging system. Calibration software processes acquired data and stores them. Processed data are further used by projection system to achieve high-precision mapping to operating surface and compensate for surface relief.

Devices of the present invention allow for the creation and unique identification of patterns in data that highlight the information of interest. The data sets in this case may be discrete images, each tightly bounded in spectra that can then be analyzed. This is analogous to looking at a scene through various colored lenses, each filtering out all but a particular color, and then a recombining of these images into something new. Such techniques as false color analysis (assigning new colors to an image that don't represent the true color but are an artifact designed to improve the image analysts by a human) are also applicable. Optionally, optics can be modified to provide a zoom function, or to transition from a micro environment to a macro environment and a macro environment to a micro environment. Further, commercially available features can be added to provide real-time or near real-time functioning. Data analysis can be enhanced by triangulation with two or more optical acquisition systems. Polarizers may be used as desired to enhance signatures for various targets.

In addition to having the ability to gather data, the present invention also encompasses the ability to combine the data in various manners including vision fusion, summation, subtraction and other, more complex processes whereby certain unique signatures for information of interest can be defined so that background, data and imagery can be removed, thereby highlighting features or information of interest. This can also be combined with automated ways of noting or highlighting items, areas or information of interest in the display of the information.

The hyperspectrally resolved image in the present invention is comprised of a plurality of spectral bands. Each spectral hand is adjacent to another forming a continuous set. Preferably, each spectral baud having a bandwidth of less than 50 nm, more preferably less than 30 nm, more preferably less than 20 nm, more preferably, from about 20-40 nm, more preferably, from about 20-30 nm, more preferably, from about 10-20 nm, more preferably from about 10-15 nm, and more preferably from about 10-12 nm.

It is clear to one skilled in the art that there are many uses for a medical hyperspectral imager (MHSI) according to the invention. The MHSI offers the advantages of performing the functions for such uses faster, more economically, and with less equipment and infrastructure/logistics tail than other conventional techniques. Many similar examples can be ascertained by one of ordinary skill in the art from this disclosure for circumstances where medical personal relies on their visual analysis of the biological system. The MHSI acts like "magic glasses" to help human to see inside and beyond.

Algorithm Description

Figure 2:
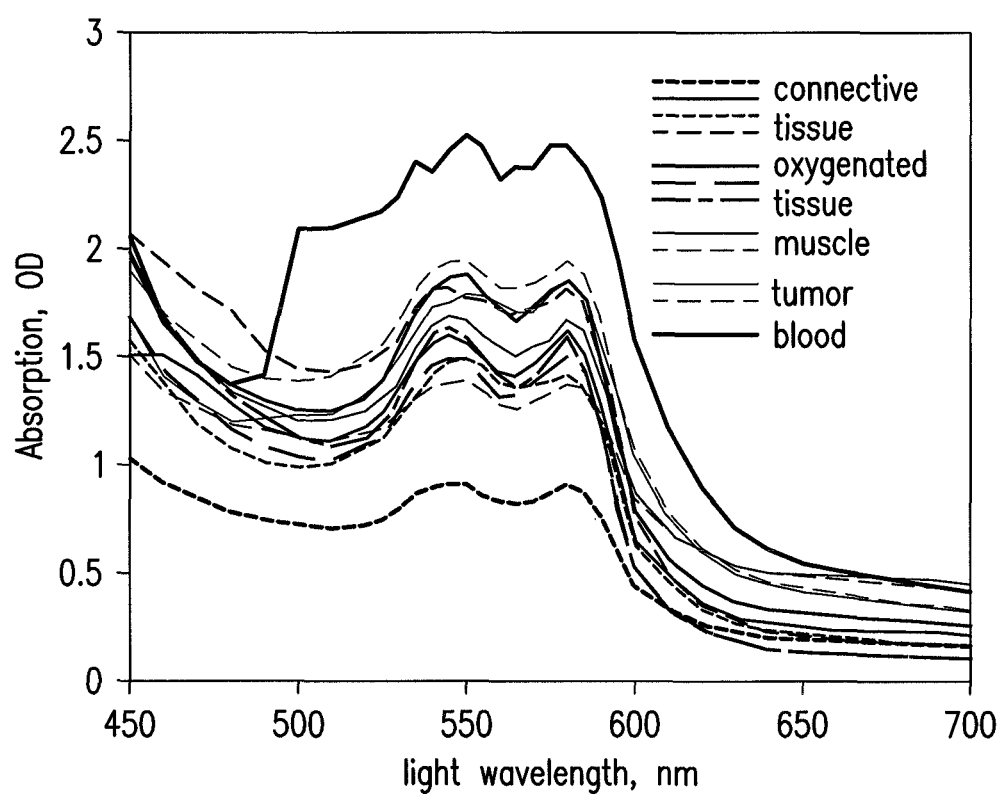
FIG. 2: Absorption spectra in the visible light wavelength range from different tissue types as recorded, by a single pixel on an image recording devise.
Figure 3:
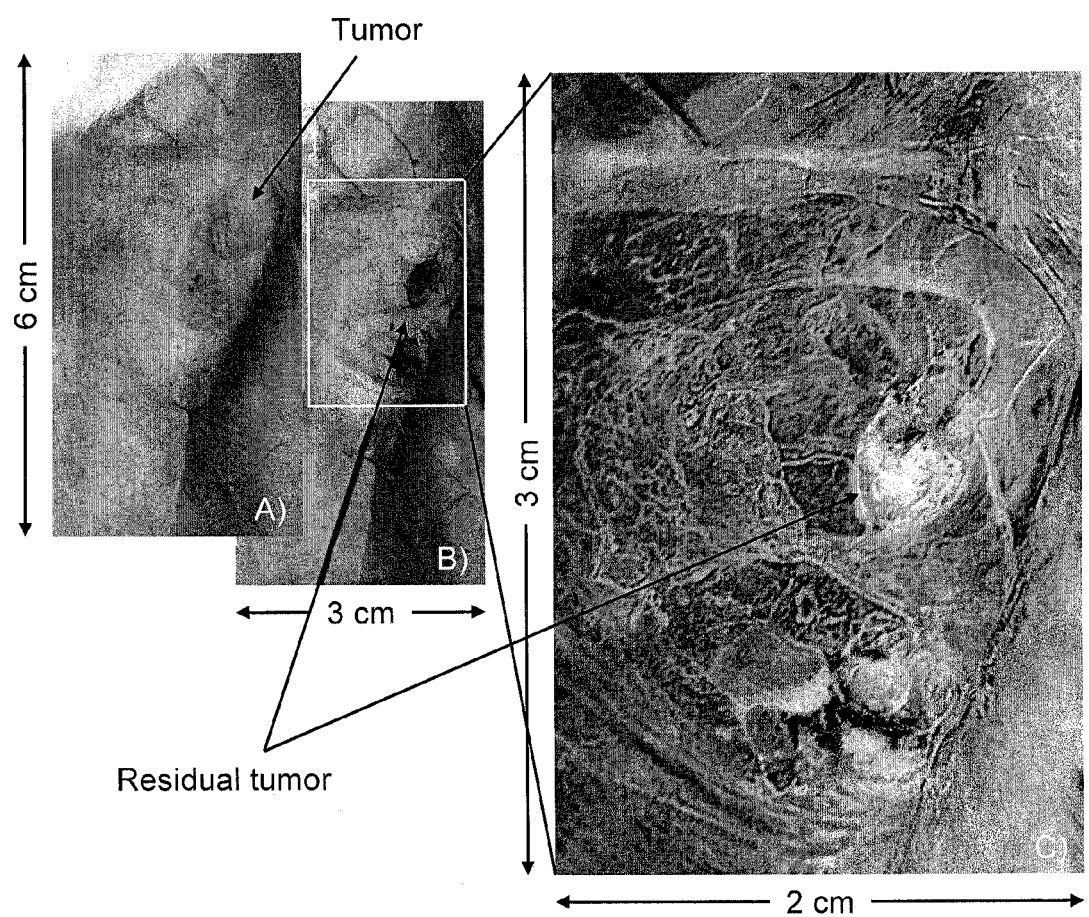
FIG. 3: A sequence of images comparing color pictures of the operation site, where (A) is the field of view as seen by surgeon, (B) is a slight magnification to show residual tumors intentionally left in the tamer bed, and (C) is the hyperspectral solution image. MHSI identifies different tissue types for the surgeon by displaying results of the algorithm using pseudo-color images (C) that highlight and amplify visibility of tumor tissue.

The embodiment of cancer detecting algorithm Involves the following steps:

1. Preprocess the HSI data. Preferably, by removing background radiation by subtracting the calibrated background radiation from each newly acquired image while accounting for uneven light distribution by dividing each image by the reflectance calibrator image and registering images across a hyperspectral cube.
2. Build a color-photo-quality visual image. Preferably, by concatenating three planes from the hyperspectral cube at the wavelengths that approximately correspond to red (preferably in the range of about 580-800 nm, more preferably in the range of about 600-700 nm, more preferably in the range of about 625-675 nm and more preferably at about 650 nm), green (preferably in the range of about 480-580 nm, more preferably in the range of about 500-550 nm, more preferably in the range of about 505-515 nm, and more preferably at about 510 nm), and blue (preferably in the range of about 350-490 nm, more preferably in the range of about 400-480 nm, more preferably in the range of about 450-475 am, and more preferably at about 470 nm) color along the third dimension to be scaled for RGB image.
3. Define a region of interest (ROI). Preferably, where the solution is to be calculated unless the entire field of view to be analysed.
4. Convert all hyperspectral image intensities into units of optical density. Preferably, by taking the negative logarithm of the decimal base. FIG. 2 shows examples of spectra taking from single pixels at different tissue sites within an image. Tissue sites include connective tissues, oxygenated tissues, muscle, tumor, and blood,
5. Decompose the spectra for each pixel (or ROI averaged across several pixels). Preferably, decompose into several independent components, more preferably, two of which are oxyhemoglobin and deoxyhemoglobin,
6. Determine three planes for RGB pseudo-color image. Preferably, determine by using characteristic features of the spectra. Preferably, the red plane is a slope coefficient for the blue portion of the spectra (wavelengths shorter than about 500 nm) at each pixel; the green and blue planes are the offset and the slope coefficients for the red portion of the spectra (starting from about 640 nm and longer) at each pixel. More preferably, coefficients for oxy and deoxy components (or other components of spectral decomposition), or their combination may be used to define the red, green, and blue planes. More preferably, a combination of the spectral images at different wavelengths, for example the ratio (or difference) between a wavelength in the red region (preferably in the range of about 580-800 nm, more preferably in the range of about 600-700 nm, more preferably in the range of about 625-675 nm and more preferably at about 650 nm) and a wavelength in the yellow (preferably in the range of about 550-580 ran, more preferably in die range of about 555-575 nm, more preferably in the range of about 560-570 nm, and more preferably at about 565 nm) or in the orange (preferably in the range, of about 580-615 nm, more preferably in the range of about 585-610 nm, more preferably in the range of about 590-605 nm, more preferably in the range of about 595-605 nm, and more preferably at about 600 nm) regions may be used.
7. Determine a sharpness factor plane. Preferably, by using a combination of the images at different wavelengths. In one embodiment, taking a ratio of a yellow plane (preferably in the range of about 550-580 nm, more preferably in the range of about 555-575 nm, more preferably in the range of shout 560-570 nm, and more preferably at about 565 nm) to a green plane (preferably in the range of about 480-580 nm, more preferably in the range of about 500-550 nm, more preferably in the range of about 505-515 nm, and more preferably at about 510 nm) was used. In another embodiment, a combination of oxyhemoglobin and deoxyhemoglobin spectral components as a sharpness factor plane was used. In yet another embodiment, a combination of the spectral images at different wavelengths, for example, the ratio (or difference) between a wavelength in the red region (preferably in fee range of about 580-800 nm, more preferably in the range of about 600-700 nm, more preferably in the range of about 025-675 nm and more preferably at about 650 nm) and a wavelength in the yellow (preferably in the range of about 550-580 nm, more preferably. In the range of about 555-575 nm, more preferably in the range of about 560-570 nm, and more preferably at about 565 nm) or in the orange (preferably in the range of about 580-615 nm, more preferably in the range of about 85-610 nm, more preferably in the range of about 590-605 nm, more preferably in the range of about 595-605 nm, and more preferably at about 600 nm) regions was used,
8. Convert RGB Image to hue-saturation-value/intensity (HSV/I) image and scale the value (or intensity) plane with the sharpness factor plane. Convert HSV/I back to RGB image.
9. Remove outliers, in the resulting image, defining an outlier as color Intensity deviating from a typical range beyond certain number of standard deviations, preferably three. Stretch the resulting image to fill entire color intensity range, e.g. between 0 and 1 for a double precision image,
10. Display ROI in pseudo-colors. Preferably, in combination with the color photo image of die subject, or preferably, in addition to the color photo image of the subject, or more preferably, by projecting the pseudo-color image onto the observed surface. FIG. 3, Panel C shows an illustrative example of a MHSI image. The algorithm used for this image is based on analysts of the absorption spectra in the visible light wavelength range (see example of spectra in FIG. 3). Subtle changes in small blood vessel oxygen saturation are clearly demonstrated. Highly oxygenated tissue, appears bright red on the MHSI images whereas extravasating blood is black. Muscle appears green. Connective tissue appears brown with variations from yellow-orange to green or purple, depending on underlying muscle and tissue oxygen saturation. The tumors have been colorized as cyan to clearly stand out for obvious identification by the surgeon. The location of residual tumor can be conveyed to the surgeon by projecting the pseudo-color image or some variance such as a binary image of the residual tumor directly onto the tumor bed. Additional information can be conveyed through images portraying the oxyhemoglobin, deoxyhemoglobin, slope and offset coefficients, or any linear or nonlinear combination such as the oxyhemoglobin to deoxyhemoglobin ratio.

11. Characterize the metabolic state of the tissue of interest (e.g. tumor grade, hematoma age, connective tissue density, etc). Preferably, by using the saturation and/or intensity of the assigned color and provide a qualitative color scale bar.

As is clear to a person of ordinary skill in the art one or more of the above steps in the algorithm can be performed in a different order or eliminated entirely and still produce adequate and desired results. Preferably, the set of instructions includes only the steps of preprocessing, the hyperspectral information, building a visual image, using the entire field of view, converting all hyperspectral image intensities into units of optical density by taking a negative logarithm of each decimal base, and characterizing a metabolic state of the tissue of interest. More preferably, the set of instructions comprises preprocessing the hyperspectral information, defining a region of interest of the tissue, and characterizing a state of the tissue of interest.

Another preferred embodiment entails reducing the hyperspectral data in the spectral dimension into a small set of physiologic parameters involves resolving the spectral images into several linearly independent, images (e.g. oxyhemoglobin, deoxyhemoglobin, an offset coefficient encompassing scattering properties and a slope coefficient) in the visible regime. Another embodiment determines four images (e.g. oxyhemoglobin, deoxyhemoglobin, offset/scattering coefficient, and water absorption) in the near infrared region of the spectrum. As an example for the visible region of the spectrum, linear regression fit coefficients $c1$, $c2$, $c3$ and $c4$ will be calculated for reference oxy-Hb, deoxy-Hb, and MS spectra, respectively, for each spectrum ($S_{ij}$) in an image cube:

$$\vec{S}_{ij} = \|c_1 \overrightarrow{OxyHb} + c_2 \overrightarrow{DeoxyHb} + c_3 \overrightarrow{Offset} + c_4 \overrightarrow{Slope}\|_2$$

Individual images of the oxyhemoglobin and deoxyhemoglobin components, the slope and offset or any combination, linear or nonlinear, of these terms, for example the oxy- to deoxyhemoglobin ratio, can be presented in addition to producing the pseudo-colored image to the user. This method is particularly useful for assessing microvascular changes in tissue such as in the lymphoma application.

Figure 4:
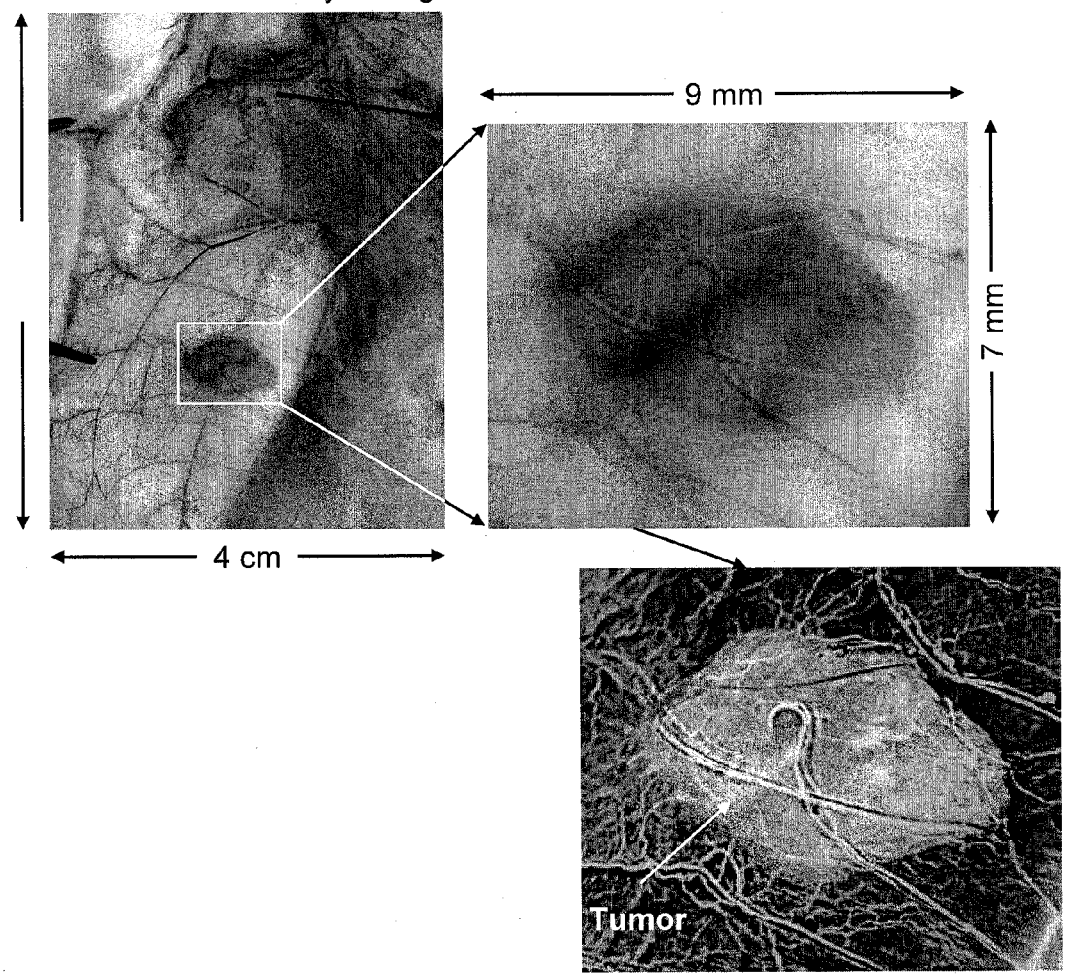
FIG. 4: Forty (40) micron resolution was available via real time digital zoom immediately after image acquisition from, a stationary MHSI device placed over the surgical field (see FIG. 1, 4 cm×6 cm field of view), enabling the operating surgeon to review images on the MHSI computer screen during the procedure to obtain an indication of tissue type (tumor vs. normal) and to evaluate surrounding microvasculature.

During breast cancer surgery, the surgeon opens up the surgical site and visually observes the area where blown or suspected tumor grows. The hyperspectral imaging system, will also acquire data, and preferably within a minute produce color and pseudo-color images of the site in question, where tissue is colorized according to its composition and viability (e.g., oxygen saturation) with tumors specifically highlighted. The medical team visually evaluates the extent of the disease taken into account the information presented in the hyperspectral image, then they decide what areas are affected by the tumor and to what degree. The surgeon excises the suspicions tissue. FIG. 4 shows an example of a tumor with MHSI image prior to excision.

Following excision, standard practice would Involve taking samples of the surrounding tissue typically at the margins of the tumor resection site, which are sent for histopathologic evaluation to assess the presence of residual cancerous cells. This process is time consuming and can take up to two-hours. "Frozen sections" of tissue from the margins are performed at randomly chosen sites and a preliminary diagnosis of presence or absence of residual tumor is made. If residual tumor is found by this method, resection of additional tissue is undertaken at the time of original surgery. The resected margins are also placed in formaldehyde and sent for "permanent section" which is more likely to provide an accurate diagnosis. If tumor is found on permanent section, when it was not found on frozen section, the patient is brought back to the operating room for additional surgery.

Figure 5:
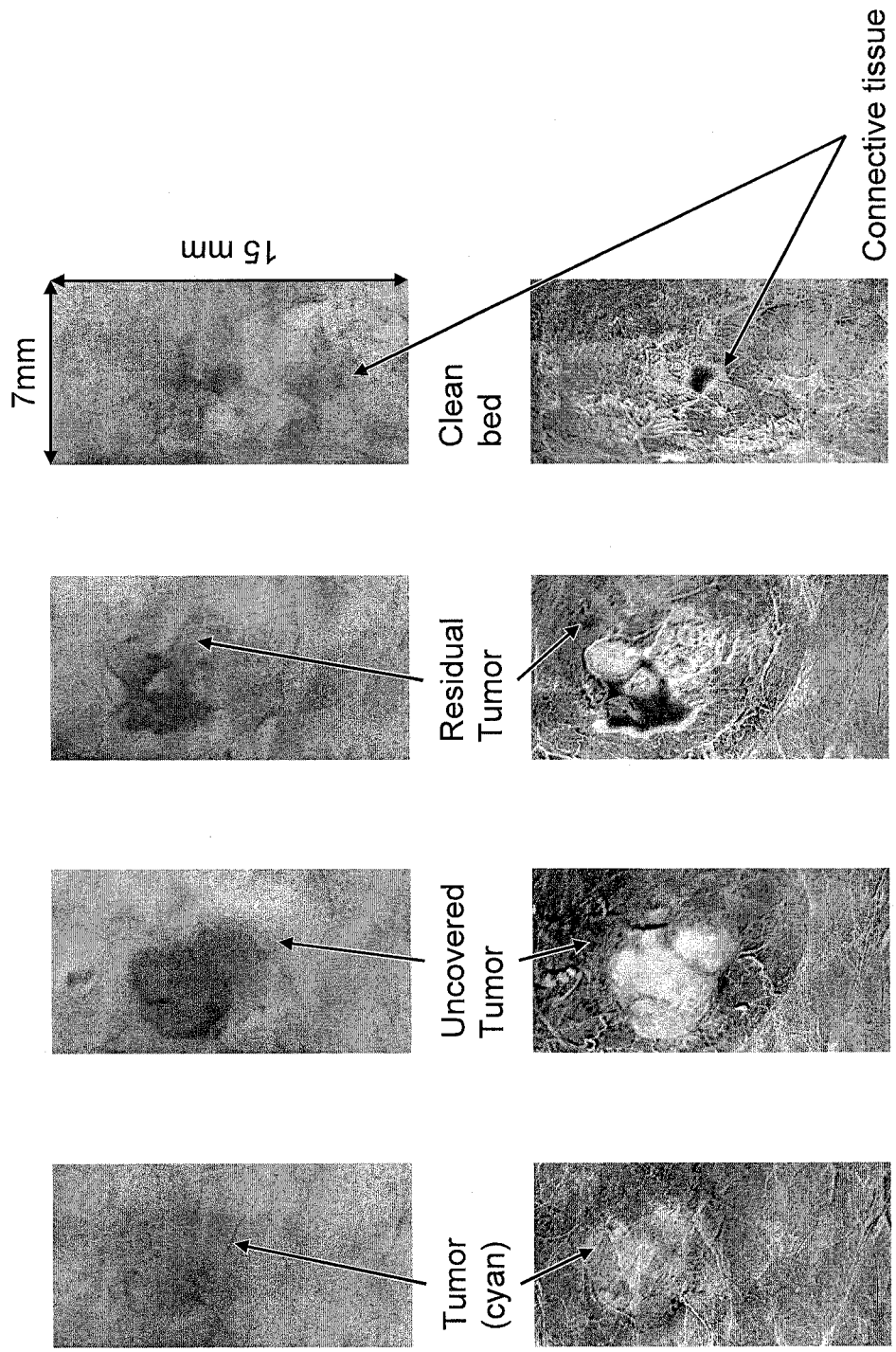
FIG. 5: MHSI Images were taken of undisturbed tumors (A, cyan structures), exposed tumors (B, bright cyan masses), small residual tumors intentionally left in bed for easy interpretation (C, bright cyan masses with black blood), and tumor beds after complete resection (D, red, purple, and greenish connective tissue areas). Details of the micro vasculature are highlighted by the HyperMed algorithm and displayed using pseudo-colors.

This embodiment describes a method where within two minutes a set of hyperspectral data are collected from the region around a resected tumor and MHSI images produced that evaluate the presence of cancer in the exposed surfaces of the rumor resection bed. If there is residual tumor left or uncovered, the surgery team will be able to detect the latter within 2 minutes of resection, and either send targeted pieces of tissue to pathology to confirm the diagnosis of residual tumor prior to excising additional tissue or continue excising until the tumor bed is clean. The MHSI is capable of examining the entire excisional wound bed which may be important for locating small, nests of tumor cells (under 0.5 mm) unlike the random. 4- or 5-point biopsy approach. Such residual tumor will be detected at once with MHSI at the time of operation. FIG. 5 shows an example of this concept. Including MHSI images of the tumor, prior to uncovering, after uncovering, after the initial resection, and from a clean wound bed.

Additionally, evaluation of lymph nodes for tumor Involvement at the time of surgery or potentially through the skin is possible with similar techniques. Similar techniques are applied to the assessment of resection margins with other cancers such as gastrointestinal (stomach, colon, etc) gynecologic (cervical, ovarian, etc) urologic (prostate, renal cell) and other forms of cancer.

HSI can be placed in similar probes endoscopically, including but not limited to, laparoscopically, thoracoscopically, cystoscopically, hysteroscopically, bronchoscopically, and mediastinoscopically to assess presence of tumor, adequacy of surgical resection or nodal or intracavitary spread.

Similar techniques are used endoscopically for the primary detection of tumors of the GI tract and to define adequacy of resection or recurrence. The pseudocolor images delivered would facilitate easy and rapid tumor identification, classification of polyps, evaluation of Barrett's esophagus or identification and evaluation of both surface and submucosal processes.

Figure 6:
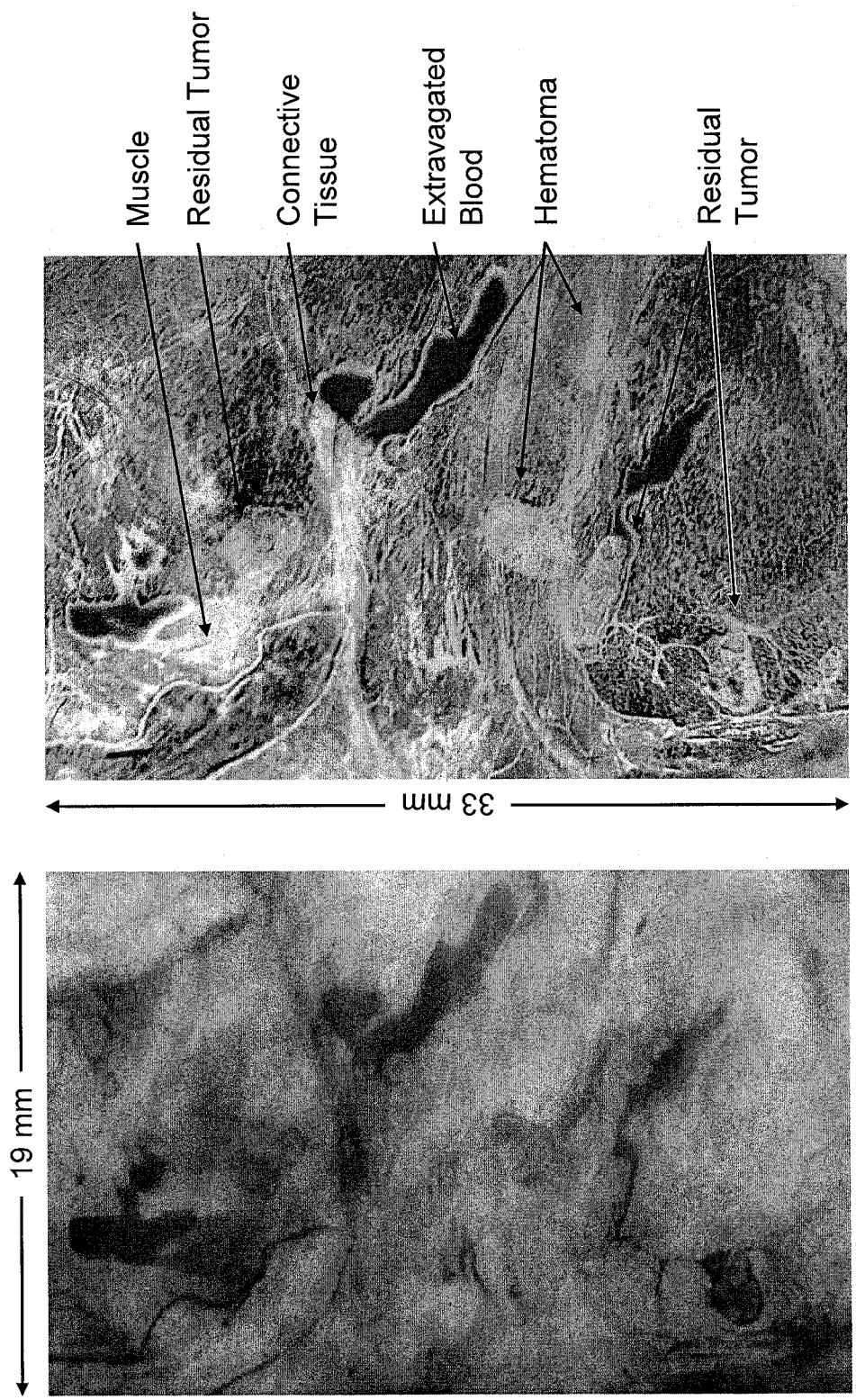
FIG. 6: MHSI distinguishes hematoma from tumor. Hematoma and extravasated blood (red/pink/orange in left panel) are often visually indistinguishable from residual tumor to the eye of the surgeon or in a simple color picture, whereas in the HyperMed MHSI pseudo-color image (right panel) blood is seen as black, oxygenated tissue as pink, and residual tumor as cyan-blue masses.

MHSI Images Allow Tissue Identification, Tumor Grade Separation, and In-Vivo Histology FIG. 6 shows illustrative MHSI Images (color and pseudo-color images) that distinguishes hematoma from tumor. Hematoma and extravasated blood (red/pink/orange in left panel) are often visually indistinguishable from residual tumor to the eye of the surgeon, or in a simple color picture, whereas in the MHSI pseudo-color image (right panel) blood is seen as black, oxygenated tissue as pink, and residual tumor as cyan-blue masses. Examples of tissue types identified in this image include muscle, residual tumor, connective tissue, extravasated blood, and a hematoma.

Since pseudo colors in the MHSI images are determined from the tissue absorption spectra, any variations in the metabolic state (no matter how small) will be reflected through gradation in the color. The tumors generally are graded by histo-pathologists according to the following classification:

| 0 | 1 | 2 | 3 | 4 |
|---|---|---|---|---|
| normal tissue | benign tumor | intraductal carcinoma | papillary and cribriform carcinoma | papillary & cribriform carcinoma with invasion and/or comedo carcinoma areas |

Figure 7:
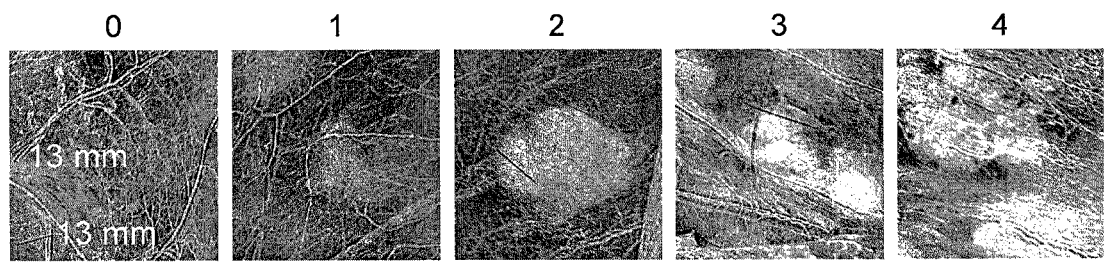
FIG. 7: MHSI images of tissue representative of each group graded front normal (grade 0) to carcinoma with invasion (grade 4). Scale for each image is 13-by 13 mm. Normal tissue (grade 0) is shown on left panel. The benign tumor and intraductal carcinomas (grades 1 and 2) have similar blue-purple masses; typically benign tumors (I) have smaller size than the intraductal carcinomas (middle panel). More advanced carcinomas: papillary and cribriform (grade 3) and carcinoma with invasion (grade 4) are represented by a cyan color with masses of solid color where internal structure of the tumor seems dense and does not show the details (last two panels).

FIG. 7 shows representative images for each grade, starting from normal tissue (left image) and progressing to grade 4 (right image).

Figure 8:
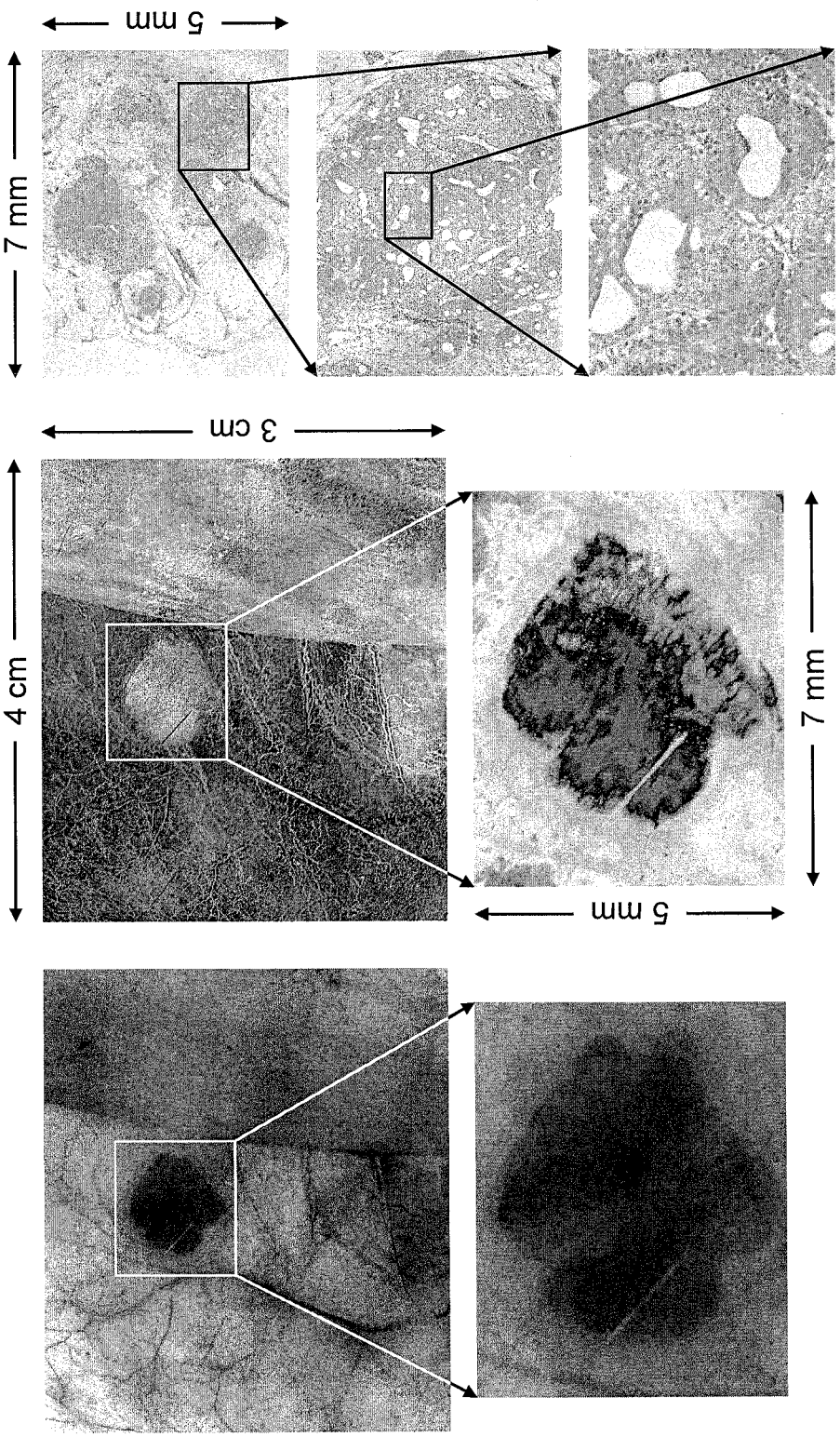
FIG. 8: MHSI highly correlated with histology, MHSI image from tumor in situ (4×3 cm) was collected by surgeon. Resected tumor and surrounding tissue (5×7 mm) was evaluated by histopathology after resection. Microscopic images with further resolution are displayed. Note that histologic features are mirrored in MHSI image.

At high resolution, MHSI presents structural information that is similar to information gather from histologic slides. FIG. 8 depicts an image from a tumor in situ (4×3 cm) that, was collected by the surgeon. Resected tumor and surrounding tissue (5×7 mm) was evaluated by histopathology after biopsy. Microscopic images with further resolution are displayed showing the histologic features mirrored in MHSI image. Characteristics of the invasion and the invasiveness of a tumor may actually be better appreciated in vivo by MHSI man by means of the in vitro histology previously required and may provide additional, information which are added to or are supplanted traditional histopathology in terms of defining prognosis and directing therapy.

MHSI Screening and Assessment of Lymphoma

A similar diagnostic algorithm based from MHSI images can be described for the screening and assessment of lymphoma. Lymphoma having circulating leukemic cells presents with unique symptoms, including the leukemic load or amount of leukemic cells in blood, systemic microvascular changes caused by leukemic cell clumping, and systemic development of leukemic tumor nodules, particularly in the lymph nodes and spleen. MHSI can be used to identify these changes to enable screening for the disease and monitoring the progression of the disease. It is envisioned that disease progression can be monitored during therapy such that the management can be tailored for the individual's response to therapy.

Figure 9A:
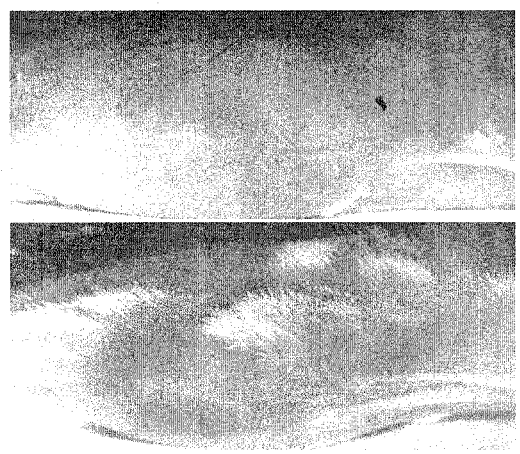
FIG. 9 Panel A: Standard visible images of side of control mouse, upper panel and mouse with late stage lymphoma (8 days post transplant), lower panel. Note small darker region representing spleen in control mouse and much larger spleen in lymphomatous mouse. Mice had undergone local chemical hair removal 24 hours prior hut residual patch of hair in lymphomatous mouse remains which obscures MHSI measurement in Panel B. Panel B: Spectra representing marked differences in all tissues examined in lymphomatous (solid) and control (dotted) mice. Panel C: Colorized MHSI images reporting oxyhemoglobin, deoxyhemoglobin, total hemoglobin and tissue oxygen saturation. Control mouse is above and lymphomatous mouse is below. Note marked decrease in oxyhemoglobin, deoxyhemoglobin, and total hemoglobin in skin of lymphomatous mouse and similar although lesser changes in the spleen. Note also nodular region in spleen which may represent lymphomatous nodule—in the proposed work we will be able to correlate these findings with histopathology at autopsy.
Figure 9B:
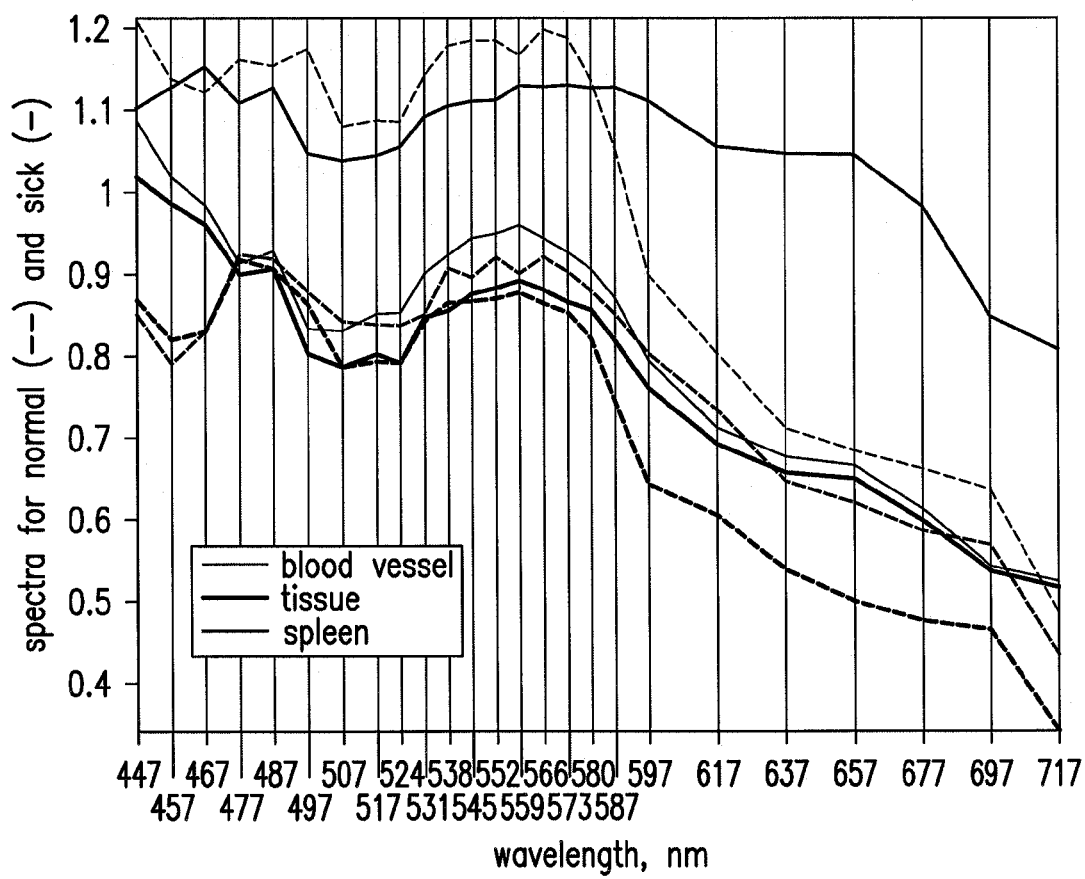
Figure 9C:
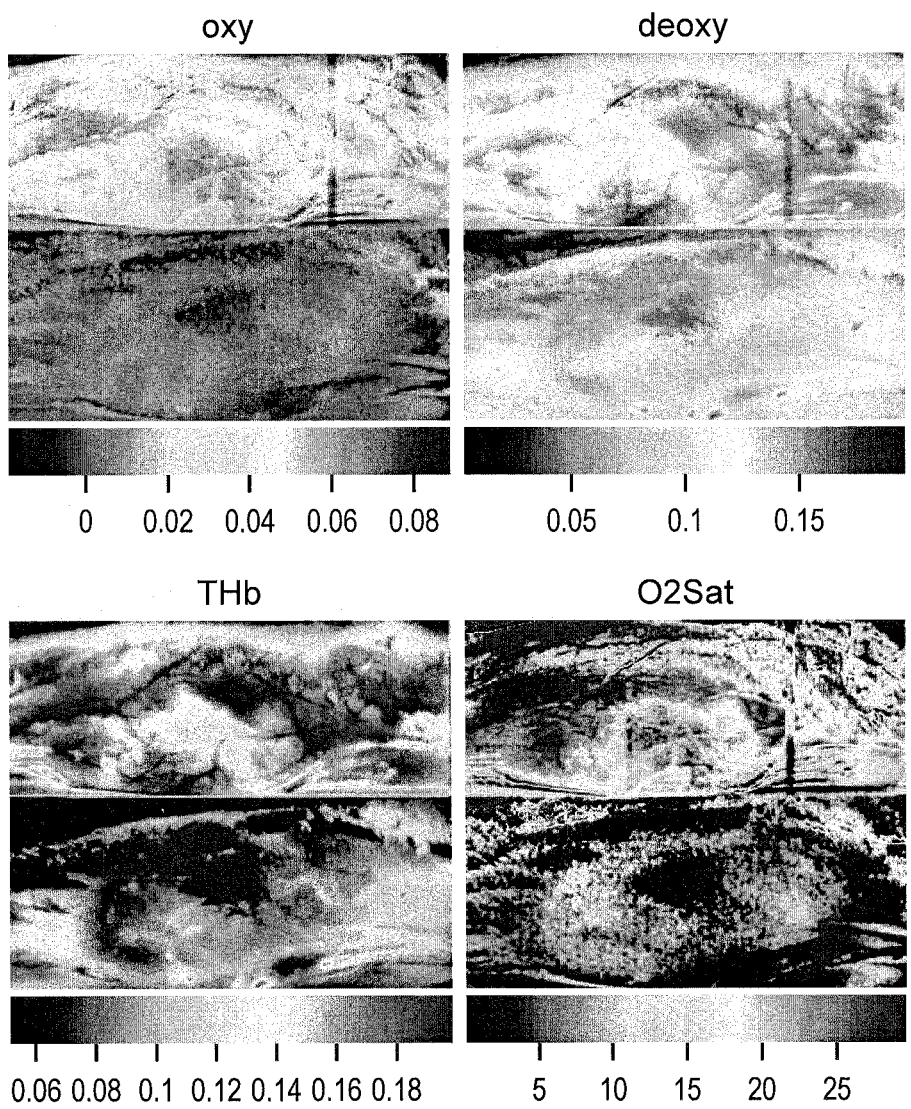

Uses of MHSI for lymphoma include imaging the lymph nodes or spleen visualized through the skin, or during endoscopic or open surgical procedures in order to assess the progression of the disease by evaluating the size of the spleen and number or density of rumor nodules. FIG. 9 shows MHSI taken through the skin of a mouse with and without lymphoma. Color images along with MHSI images of oxyhemoglobin, deoxyhemoglobin, total hemoglobin and oxygen saturation are presented from a disease and normal mouse. The change in the size of the spleen is noted in the color image as well as an increase in nodularity in the pseudo-color image of the disease mouse when compared to the normal control mouse.

Figure 10A:
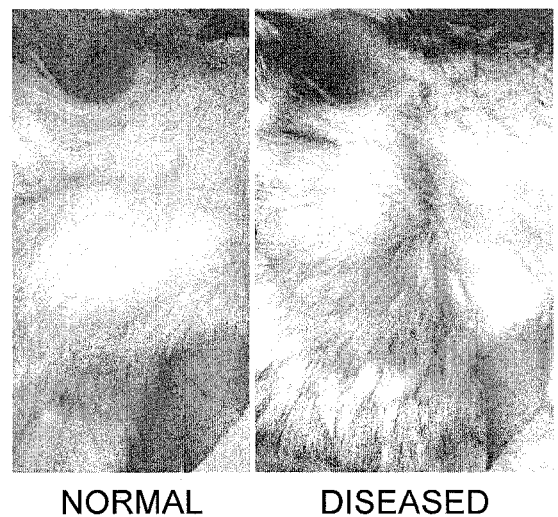
FIG. 10 Panel A: Standard visible images of head of control mouse (left panel) and mouse with late stage lymphoma (right panel; 8 days post-transplant). Panel B: Spectra representing marked differences in all tissues examined in lymphomatous (solid) and control (dotted) mice. Panel C: Colorized MHSI images reporting oxyhemoglobin, deoxyhemoglobin total hemoglobin and tissue oxygen saturation of head of mice from visible images above. Only relevant areas are ears and eyes, because remainder of head is covered by hair. Note marked decrease in oxyhemoglobin and oxygen saturation in eye, ear skin and blood vessels in lymphomatous mouse. There are similar but much less marked differences in deoxy and total hemoglobin images. These changes are consistent with both a decrease in red cell volume and in a decrease in flow with greater oxygen extraction by the tissue. A tumor signature for lymphoma is able to be defined within the ear vessels.
Figure 10B:
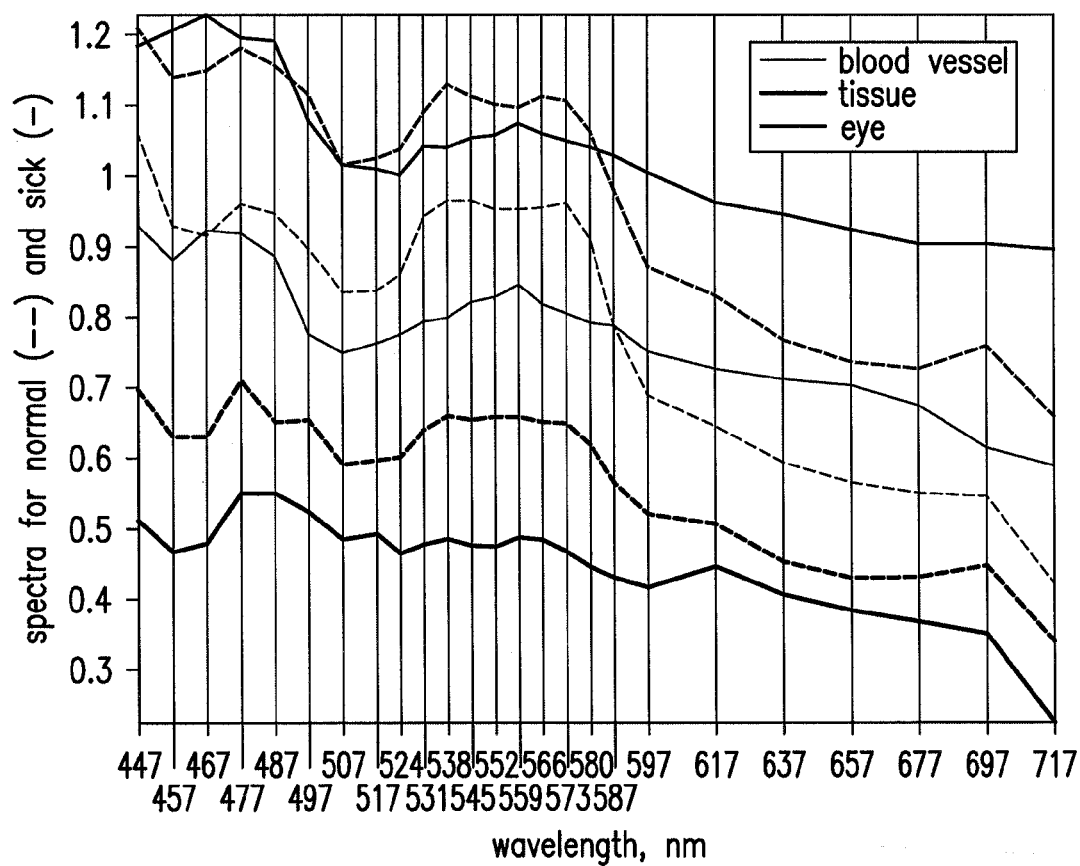
Figure 10C:
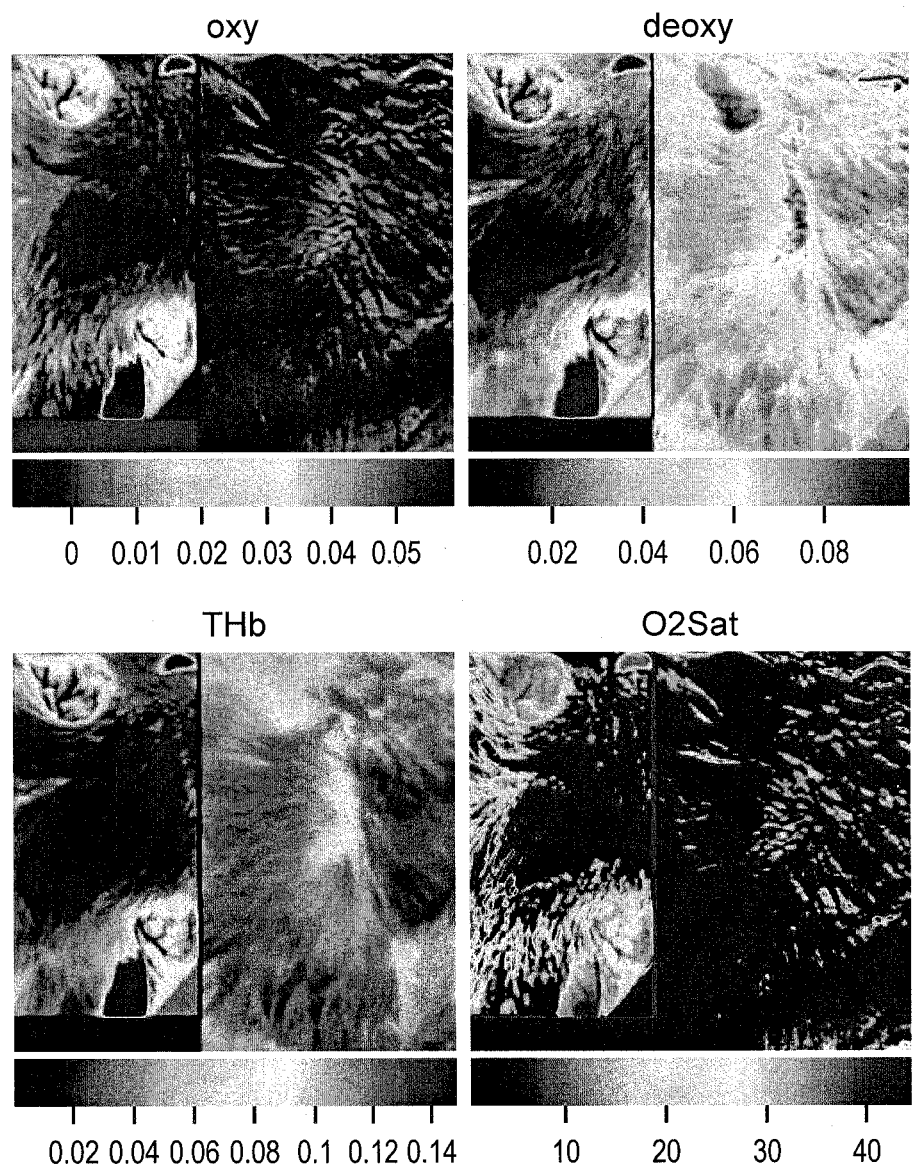

Disease progression can also be monitor with MHSI by visualizing microvascular changes in the skin and eye, or other vascular sites such as the ear, lips, oral mucosa, and tongue. FIG. 10 shows examples of microvascular changes noted from the ear and eye of a diseased and normal mouse. Color images along with MHSI images of oxyhemoglobin, deoxyhemoglobin, total hemoglogin and oxygen saturation are presented from a disease and normal mouse. A marked decrease in oxyhemoglobin and oxygen saturation in eye, ear skin and blood vessels in lymphomatous mouse is seen when compared to a normal mouse. There are similar but much less marked differences in deoxy and total hemoglobin images. These changes are consistent with both a decrease in red cell volume and in a decrease in flow with greater oxygen extraction, by the tissue.

It is also envisioned that disease progression using similar algorithms can be monitored in small and large animals as a means for developing and optimising new therapeutic agents for curing this disease.

The evaluation of other leukemias and hematogenous cancers as well as involvement of lymph nodes, solid organs and other tissue by other lymphomas, other cancers and other tumors can also be undertaken by similar techniques and will be apparent to those skilled in the art.

Other embodiments and uses of the invention will be apparent to those skilled in the art from consideration of the specification and practice of the invention disclosed, herein. All references cited herein, including all publications, U.S. and foreign patents and patent applications, are specifically and entirely incorporated by reference. It is intended, that the specification and examples be considered exemplary only.

REFERENCES CITED

[1] CA: A Cancer Journal for Clinicians; Cancer Statistics, 2005, 55:10-30 January/February.

[2] National Cancer Database

[3] Fisher B. Anderson S. Bryant J. Margolese E C. Deutseh M. Fisher E R. Jeong J H. Wolmark N. Twenty-year follow-up of a randomized trial comparing total mastectomy, lumpectomy, and lumpectomy plus Irradiation for die treatment of invasive breast cancer. New England Journal of Medicine, 347(16):1233-41, 2002 Oct. 17

[4] Singletary, S. Eva, "Surgical margins in patients with early stage breast cancer treated wife breast conservation therapy" The American Journal of Surgery 2002; 184:383-393.

[5] Frazier T G, Wong R W, Rose D: Implications of accurate pathologic margins in the treatment of primary breast cancer. Arch Surg 124:37-38, 1989

[6] Hansen N M, Grube B J, Giuliano, A E The time has come to change the algorithm for the surgical management of early breast cancer. Archives of Surgery. 137(10): 1131-5, 2002 October.

[7] Gibson G R. Lesnikoski B A. Yoo J. Mott L A. Cady B. Barm R J Jr. A comparison of ink-directed and traditional whole-cavity re-excision for breast lumpectomy specimens with positive margins. Annals of Surgical Oncology, 8(9):693-704, 2001 October.

[8] National Cancer Institute [http://www.nci.nm.gov/cancer_information].

[9] Weeks J C, Yeap B Y, Canellos G P, Shipp M A. Value of follow-up procedures in patients with large cell lymphoma, who achieve a complete remission. *J. Clin. Oncol.* 1991; 9:1190-4203.

[10] Colamsso P, Kidder L H, Levin I W, et al Infrared spectroscopic imaging: from planetary to cellular systems, Appl Spectrosc 1998; 52; 106A-120A. Treado P J, Morris M B. Appl Spectrosc Rev 1994; 29:1-38.

[11] Riaza, A, Sirohl, P, Beisl, U, Hausold, A, Muller, A., Spectral mapping of rock weathering degrees on granite using hyperspectral DAIS 7915 spectrometer data, IJ of Applied Earth Observation and Geoinformation, January 2001

[12] Thenkabail, P S, Smith, R E, De Pauw, E Hyperspectral Vegetation Indices and Their Relationships with Agricultural Crop Characteristics Volume 71, Issue 2, February 2000, Page 158-182

[13] Bowles, J H. J A. Antoniades, M M. Baumbaok, J M. Grossmann, D. Haas, P J Palmadesso and J. Stracka. (1997). Real-time analysis of hyperspectral data sets using NRL's ORASIS algorithm. Proc. SPIE Vol. 3118, p, 38-45

[14] Tran C D. Development and analytical applications of multispectral imaging techniques: an overview. Fresenius J Anal Chem 2001 February; 36913-4):313-9

[15] Sowa M G, TR. Mansfield. M. Jackson, J. C. Docherty, R. Deslauriers, find H. H. Mantsch. "FT-IR/NIR Assessment of Ischemic Damage ic the Rat Heart" *Mikrochimca Acta [suppl.]*, 1997, 14, 451-453.

[16] Doornbos R M, Lang R, Aalders M C, Cross F W, Sterenborg H J. The determination of in vivo human tissue optical properties and absolute chromophobe concentrations using spatially resolved steady-state diffuse reflectance spectroscopy. Phys Med Biol 1999 April; 44(4):967-81.

[17] Zonios G, Bykowski J, Kollias N. Skin melanin, hemoglobin, and light scattering properties can be quantitatively assessed in vivo using diffuse reflectance spectroscopy. J Invest Dermatol 2001 December; 117(6): 1452-7.

[18] Freeman, et al. Medical Hyperspectral Imaging (MHSI) of 1,2-dimethylbenz(a)-anthracene (DMBA) Induced Breast Tumors In Rats. San Antonio Breast Cancer Symposium, 2004

[19] Cancio, L. C; Brand, D; Kerby, J; Freeman, J; Hopmeier, M; and Mansfield, J. R. "Visible Hyperspectral Imaging; Monitoring the Systemic Effects of Shock and Resuscitation." Proc SPIE 4614:155), 2002.

[20] Panasyak S V, Freeman I E, Cooke W, Hopmeier M, Converimo V. Initial Demonstration in Human Subjects of Medical Hyperspectral Imaging (MHSI) as a Novel Stand-Off Non-Invasive Method for Diagnosing and Measuring Hemodynamic Collapse. Accepted for American Association of Shock and Trauma Annual Meetings 2005.

[21] Freeman J E, Panasyuk S V, Hopmeier M J, Lew R A, Batchinski A, Cancio L C. Evaluation of New Methods of Hyperspectral Image Analysis for the Diagnosis of Hemorrhagic Shock. Accepted for American Association of Shock and Trauma Annual Meeting, 2005.

[22] Greenman R L, Panasyuk S, Wang X, Lyons T E, Dinh T, Langoria L, Giurini J M, Freeman J, Khaodhiar L, Veves A. Early changes in the skin microcirculation and muscle metabolism of the diabetic foot Lancet 2005; 366: 1711-17.

The invention claimed is:

1. A multispectral or hyperspectral medical imaging system comprising:
a plurality of LED lights, each respective LED light in the plurality of LED lights configured to emit radiation at a particular spectral band in a plurality of spectral bands used by a diagnostic protocol module;
a first stage optic configured to receive radiation projected, from one or more respective LED lights in the plurality of LED lights, off of an in vivo tissue located at a region of interest on a subject;
one or more polarizers in optical communication with the first stage optic;
an imaging sensor for recording an image of the radiation projected off of the in vivo tissue;
a diagnostic protocol module adapted to detect a particular characteristic of the in-vivo tissue;
a diagnostic processor configured to:
switch one or more respective LED light in the plurality of LED lights off and on based on the diagnostic protocol module,
instruct the imaging sensor to record a plurality of images of the region of interest based on the diagnostic protocol module, each respective image in the plurality of images corresponding to radiation emitted at a particular spectral band by one or more respective LED light in the plurality of LED lights,
obtain a multispectrally or hyperspectrally resolved image based on the plurality of images, and
obtain a pseudo-color image of the region of interest based on the multispectrally or hyperspectrally resolved image, the pseudo-color image enhancing the visibility of the particular characteristic of the in vivo tissue present in the region of interest; and
a projection subsystem configured to project the pseudo-color image onto the region of interest, wherein the projection subsystem comprises an image projector with a field-of-view co-aligned with a field of view of the first stage optic.

2. The multispectral or hyperspectral medical imaging system of claim 1, wherein the imaging system is portable.

3. The multispectral or hyperspectral medical imaging system of claim 2, wherein the imaging system weighs less than 25 pounds.

4. The multispectral or hyperspectral medical imaging system of claim 1, wherein the plurality of LED lights is configured in a circular array about the first stage optic.

5. The multispectral or hyperspectral medical imaging system of claim 1, wherein at least one respective LED light in the plurality of LED lights is configured to emit radiation in the visible spectrum.

6. The multispectral or hyperspectral medical imaging system of claim 1, wherein at least one respective LED light in the plurality of LED lights is configured to emit radiation in the near-infrared spectrum.

7. The multispectral or hyperspectral medical imaging system of claim 5, wherein at least one respective LED light in the plurality of LED lights is configured to emit radiation in the near-infrared spectrum.

8. The multispectral or hyperspectral medical imaging system of claim 1, further comprising a first radiation filter placed in front of a respective LED light in the plurality of LED lights and a second, matching radiation filter, placed in optical communication with the imaging sensor.

9. The multispectral or hyperspectral medical imaging system of claim 1, wherein a first polarizer in the one or more polarizers is placed in front of a respective LED light in the plurality of LED lights and a second polarizer in the one or more polarizers is placed in optical communication with the first stage optic.

10. The multispectral or hyperspectral medical imaging system of claim 1, wherein the imaging sensor is configured to detect radiation in the visible spectrum.

11. The multispectral or hyperspectral medical imaging system of claim 1, wherein the imaging sensor is configured to detect radiation in the near-infrared spectrum.

12. The multispectral or hyperspectral medical imaging system of claim 10, wherein the imaging sensor is configured to detect radiation in the near-infrared spectrum.

13. The multispectral or hyperspectral medical imaging system of claim 1, wherein the diagnostic processor is further configured to provide an output to a video display.

14. The multispectral or hyperspectral medical imaging system of claim 13, wherein the video display is contained within the multispectral or hyperspectral medical imaging system.

15. The multispectral or hyperspectral medical imaging system of claim 1, further comprising a communication interface in electrical communication with the diagnostic processor.

16. The multispectral or hyperspectral medical imaging system of claim 1, wherein each respective spectral band in the plurality of spectral bands used by the diagnostic protocol module has a bandwidth of less than 20 nm.

17. The multispectral or hyperspectral medical imaging system of claim 1, wherein the particular characteristic of the in vivo tissue enhanced by the pseudo-color image is cancerous tissue.

18. The multispectral or hyperspectral medical imaging system of claim 17, wherein the cancerous tissue comprises breast cancer or lymphoma.

19. The multispectral or hyperspectral medical imaging system of claim 1, wherein the pseudo-color image includes information about at least one of the presence of a tumor, the presence of a residual tumor at a margin of a surgical excision bed, and the progression of a tumor.

20. The multispectral or hyperspectral medical imaging system of claim 19, wherein the information about the progression of the tumor includes at least one of tumor stage grading and microvascular changes in a vascular tissue.

* * * * *